(12) United States Patent  
Feldchtein et al.

(10) Patent No.: US 7,728,985 B2  
(45) Date of Patent: Jun. 1, 2010

(54) POLARIZATION-SENSITIVE COMMON PATH OPTICAL COHERENCE REFLECTOMETRY/TOMOGRAPHY DEVICE

(75) Inventors: Felix I. Feldchtein, Cleveland, OH (US); Valentin M. Gelikonov, Nizhny (RU); Grigory V. Gelikonov, Nizhny (RU)

(73) Assignee: Imalux Corporation, Cleveland, OH (US)

( * ) Notice: Subject to any disclaimer, the term of this patent is extended or adjusted under 35 U.S.C. 154(b) by 158 days.

(21) Appl. No.: 11/559,226

(22) Filed: Nov. 13, 2006

(65) Prior Publication Data

US 2007/0109553 A1 May 17, 2007

Related U.S. Application Data

(60) Provisional application No. 60/736,534, filed on Nov. 14, 2005.

(51) Int. Cl.  
*G01B 11/02* (2006.01)

(52) U.S. Cl. ..................................................... 356/497

(58) Field of Classification Search ................. 356/479, 356/491–495, 497  
See application file for complete search history.

(56) References Cited

U.S. PATENT DOCUMENTS

| 5,555,087 A | * | 9/1996 | Miyagawa et al. | 356/485 |
| 2004/0246490 A1 | * | 12/2004 | Wang | 356/479 |
| 2005/0254060 A1 | * | 11/2005 | Alphonse | 356/479 |
| 2005/0254061 A1 | * | 11/2005 | Alphonse | 356/479 |
| 2006/0028652 A1 | * | 2/2006 | Chan et al. | 356/497 |
| 2006/0103850 A1 | * | 5/2006 | Alphonse et al. | 356/479 |

OTHER PUBLICATIONS

Gelikonov, et al., New Approach to Cross-polarized Optical Coherence Tomography Based on Orthogonal Arbitrarily Polarized Modes, Wiley InterScience, May 22, 2006, pp. 1-7.  
Abstract for Gelikonov, et al., New Approach to Cross-polarized Optical Coherence Tomography Based on Orthogonal Arbitrarily Polarized Modes, Wiley InterScience, May 22, 2006, pp. 1-7.

* cited by examiner

*Primary Examiner*—Tarifur Chowdhury  
*Assistant Examiner*—Jonathan D Cook  
(74) *Attorney, Agent, or Firm*—Renner, Otto, Boisselle & Sklar, LLP

(57) ABSTRACT

Polarization sensitive common path OCT/OCR devices are presented. Optical radiation from a source is converted into two cross-polarized replicas propagating therethrough with a predetermined optical path length difference. The two cross-polarized replicas are then delivered to an associated sample by a delivering device, which is, preferably, an optical fiber probe. A combination optical radiation is produced in at least one secondary interferometer by combining a corresponding portion of an optical radiation returning from the associated sample with a reference optical radiation reflected from a tip of an optical fiber of the optical fiber probe. Subject to a preset optical path length difference of the arms of the at least one secondary interferometer, a cross-polarized component, and/or a parallel-polarized component of the combined optical radiation, are selected. The topology of the devices allows for time domain, as well as for frequency domain registration.

17 Claims, 7 Drawing Sheets

US 7,728,985 B2

POLARIZATION-SENSITIVE COMMON PATH OPTICAL COHERENCE REFLECTOMETRY/TOMOGRAPHY DEVICE

CROSS-REFERENCE TO RELATED APPLICATIONS

This application is based on and claims priority to provisional U.S. patent application Ser. No. 60/736,534, which was filed on Nov. 14, 2005.

BACKGROUND OF THE INVENTION

The present invention relates to systems and methods for visualizing subsurface regions of samples, and more specifically, to a polarization-sensitive common path optical coherence reflectometer (OCR) and polarization-sensitive common path optical coherence tomography (OCT) device that provides internal depth profiles and depth resolved images of samples.

Optical coherence reflectometry/tomography is known to be based on optical radiation interference, which is a phenomenon intrinsically sensitive to the polarization of the optical radiation, because parallel-polarized components produce strongest interference, while cross-polarized components do not interfere at all.

As will be appreciated by those skilled in the art, the concept of "parallel-polarized" and "cross-polarized" is applied here for elliptical polarization. "Parallel-polarized" is used for components with elliptical polarizations having the same eccentricity, same orientation of the long axis (ellipse tilt angle), and same rotation direction for the electric field. "Cross-polarized" is used for components with elliptical polarizations having the same eccentricity, orthogonal orientation of the long axis, and opposite rotation direction for the electric field.

Optical coherence reflectometry/tomography typically involves splitting an optical radiation into at least two portions, and directing one portion of the optical radiation toward a subject of investigation. The subject of investigation will be further referred to as a "sample", whereas the portion of optical radiation directed toward the sample will be further referred to as a "sample portion" of optical radiation. The sample portion of optical radiation is directed toward the sample by means of a delivering device, such as an optical probe. Another portion of the optical radiation, which will be further referred to as "reference portion", is used to provide heterodyne detection of the low intensity radiation, reflected or backscattered from the sample detecting interference of the two portions and forming a depth-resolved profile of the coherence backscattering intensity from a turbid media (sample).

Therefore, almost any embodiment of OCR/OCT is, to some extent, polarization sensitive in the sense that changes in the polarization state of the optical radiation, occurring with the reference or sample portions of the optical radiation, or more generally speaking, relative changes in the polarization states of the reference and sample portions, impact the interference signal. However, it is more common to associate "polarization sensitive OCR/OCT" with embodiments allowing to assess, at some level, changes in relative polarization orientation of the reference and sample optical radiation portions and differentiate these changes from just changes in the coherence backscattering intensity. Typically, as known in the art, this is performed by creating an initial 45 degree polarization rotation between the reference and sample portions of the optical radiation and performing polarization splitting of the recombined radiation using independent photodetectors and two-channel registration. This concept requires the use of a polarization-maintaining (PM) fiber for an optical fiber implementation, because in the regular single mode fibers, stress-induced birefringence produces uncontrollable changes in the polarization state of the optical radiation. This approach successfully works, however PM fiber and elements made with PM fiber are known to be expensive and difficult to handle. Additionally, polarization crosstalk between linear eigen polarization modes of the PM fiber creates well known secondary coherence artifacts, appearing as a set of vertically shifted ghost images, being weak but visible replicas of the main OCT image.

Typically, any optical coherence reflectometer or OCT device is specified by a longitudinal (in-depth) range of interest, whereas the longitudinal range of interest and the sample overlap, at least partially. The longitudinal range of interest includes a proximal boundary and a distal boundary, and in time domain systems is equivalent to the longitudinal scanning range. In traditional time domain optical coherence reflectometry, at every moment only a small part of the sample portion of the optical radiation, reflected or backscattered from some point located inside the boundaries of the longitudinal range of interest is utilized. In-depth profiling of the sample is provided by introducing a variable optical path length difference for the sample and reference portions of the optical radiation.

A well known version of time domain optical coherence reflectometry and tomography is the "common path" version, also known as autocorrelator or Fizeau interferometer based OCR/OCT. In this version, the reference and sample portions of the optical radiation do not travel along separate optical paths. Instead, a reference reflection is created in the sample optical path by introducing an optical inhomogenuity in the distal part of the delivering device, the inhomogenuity serving as a reference reflector. Resulting from that, the reference and sample portions of the optical radiation experience an axial shift only. The distance between the reference reflector and the front boundary of the longitudinal range of interest will be considered here as "reference offset". The entire combination of the sample portion of the optical radiation and axially shifted reference portion is combined with the replica of the same combination, shifted axially, so the reference portion of one replica has a time of flight (or optical path length) matching that of the sample portion of another replica. These portions interfere in a very similar way to the traditional "separate path" time domain optical coherence reflectometry/tomography embodiments. The interference signal is formed by a secondary interferometer, the two arms of which have an optical length difference ("interferometer offset") equal to the reference offset. By scanning an optical delay between the two replicas, a time profile of the interference signal is obtained, which represents the in-depth profile of the coherent part of the reflected sample optical radiation. The later is substantially equivalent to the profile obtained in traditional separate path embodiments.

Common path reflectometry/tomography has a lot of intrinsic advantages over separate path reflectometry/tomography. These advantages are based on the fact that reference and sample portions of the optical radiation propagate in the same optical path and therefore experience substantially identical delay, polarization distortions, optical dispersion broadening, and the like. Therefore, the interference fringes are insensitive to the majority of the probe properties, including the optical fiber probe length, dispersion and polarization properties. In separate path reflectometry/tomography, the length and dispersion of the sampling arm should be closely matched with the reference arm and the polarization mismatch should be prevented (using PM fiber or other means) or compensated (using polarization diversity receiver or other means).

The optical spectrum of the combined reference and sample portions of the optical radiation, both in the separate path and the common path reflectometry and OCT designs, has all necessary information about the in-depth coherent reflection profile by including a component that is Fourier conjugate of the in-depth profile of the sample. Thus, the profile is capable of being extracted from Fourier transformation of the optical spectrum of the combined optical radiation.

Fourier transformation of the optical spectrum of the reference and sample optical radiation combination is actually well known and has been utilized in frequency domain optical coherence reflectometry and tomography (also known as spectral domain and Fourier domain) since 1995. In frequency domain optical coherence reflectometry, the reference and sample portions of the optical radiation have a substantially similar optical path. The optical spectrum of the combined optical radiation can be registered using parallel means (such as a spectrograph) or sequential scanning means using a swept frequency optical source.

Common path frequency domain optical coherence reflectometry and tomography are well known in the art. However, previously known devices typically employ an optical layout where reference reflection occurs in the vicinity of the sample. In these devices the combination of reference and sample reflection is directly spectrally analyzed without any additional optical processing, such as using an additional interferometer. This approach works very well if stable reference reflection can be obtained from a point axially close to the sample. Unfortunately, in many situations, and in particular, in a probe design for medical application it is very difficult or even impossible to obtain reference reflection from the vicinity of the sample and instead, reference reflection can only be obtained from a point located far from the sample.

A limitation to such common path frequency domain OCR/OCT systems without a secondary interferometer is very large required spectral resolution of the frequency domain OCR/OCT processing engine. This limitation becomes especially important in medical applications. The problem is that even for miniature optical fiber endoscopic probes known in the art that use the optical fiber tip of the optical fiber probe as a reference element, the reference offset could be as big as 10 mm, since the optical fiber probe inevitably includes a lens system in its distal part. This distance may be greater if a bigger probe with a larger field of view is required, such as for laparoscopy. It is known that the larger the in-depth distance is between the most remote points involved in the optical interference (which is the reference offset plus intended depth range), the finer the spectral resolution of the system should be, in order to resolve the highest frequency spectral fringes.

The later can be illustrated referring to the spectrum of two pairs of pulses with different time separation. Each pair of pulses (for OCR/OCT corresponding to a pair of reflecting surfaces separated in depth) produces interference fringes in the spectrum. The frequency of spectral fringes increases accordingly with increasing of the delay between pulses. To restore the in-depth profile, the spectral resolution of the frequency domain OCR/OCT engine should be sufficient to resolve the most frequent fringes in the optical spectrum. In spatial-temporal terminology, the effective coherence length should be sufficient to provide interference between the most distant points. Therefore, a large reference offset creates unnecessary high spectral resolution requirements for the spectrometer or unnecessary strict instantaneous line width requirements for the tunable source. It also puts an additional burden on the data acquisition and real time signal processing system, when a several times increase of data flow is required for the same image acquisition rate. Additionally, the system design would require substantial changes if another probe with different reference offset is needed. All of the described is capable of making questionable the advantage of using common path topology in a frequency domain OCR/OCT system.

One solution would be to add an additional interferometer in the manner known for time domain OCT/OCR systems. Unfortunately, applying frequency domain registration to earlier separate path OCR/OCT systems creates a serious problem, known as the "depth ambiguity problem" (also referred to as mirror artifact or depth degeneracy). The problem is well known and is associated with Fourier transformation's inability to differentiate between positive and negative depth coordinates in a case of the optical path difference for the interfering reference and sample portions of the optical radiation being reduced to zero. The same problem would arise for a common path frequency domain OCR/OCT system utilizing a secondary interferometer since in a system of this type, as discussed above, the interference signal is formed by reducing to zero the optical path difference for the interfering reference and sample portions of the two replicas of the optical radiation. There are several ways known to deal with the depth degeneracy problem, all of them being cost consuming and rather complicated for use in a medical device.

Thus, there exists a need for polarization-sensitive common path OCR/OCT devices that use the advantages of a common path optical interferometer design while overcoming limitations of previous polarization-sensitive common path OCR/OCT devices.

There also exists a need for polarization-sensitive common path OCR/OCT devices that are capable of being implemented with the use of isotropic optical fiber.

A need also exists for polarization-sensitive common path OCR/OCT devices that are insensitive to the majority of the probe properties, including the optical fiber probe length, dispersion properties and polarization mismatch.

A need also exists for polarization-sensitive common path OCR/OCT devices that are capable of being implemented with both time domain and frequency domain registration.

SUMMARY OF THE INVENTION

In accordance with the present invention, there are provided improved polarization-sensitive common path OCR/OCT devices that use the advantages of a common path optical interferometer design together with the advantages of being implemented with isotropic optical fiber.

Further, in accordance with the present invention, there are provided improved polarization-sensitive common path OCR/OCT devices providing both time domain and frequency domain registration.

Further, in accordance with the present invention, there are provided polarization-sensitive common path OCR/OCT devices that provide registration of a portion of the optical radiation depolarized by an associated sample, i.e. of a cross-polarized component of the optical radiation reflected or backscattered from an associated sample.

Still further, in accordance with the present invention, there are provided polarization-sensitive common path OCR/OCT devices that provide registration of a portion of the optical radiation not depolarized by an associated sample, i.e. of a parallel-polarized component of the optical radiation reflected or backscattered from an associated sample.

According to one aspect of the present invention, a polarization-sensitive common path optical coherence reflectometer is provided that includes a source of optical radiation and converting means optically coupled with the source of optical radiation. The converting means is adapted for producing at least two cross-polarized replicas of the optical radiation incoming from the source of optical radiation, propagating therethrough with an optical path length difference. The polarization-sensitive common path optical coherence reflectometer also includes a delivering device adapted for forming and delivering an optical radiation beam to an associated sample. The delivering device includes a proximal part and a distal part. The distal part of the delivering device includes a reference reflector. The delivering device is further adapted for producing a combined optical radiation representative of an optical radiation having returned from an associated sample. Those skilled in the art will appreciate that the combined optical radiation is a combination of an optical radiation having returned from an associated sample and of an optical radiation reflected from the reference reflector.

Also included in the reflectometer of the subject application is a directional element optically coupled with the converting means and optically coupled with the proximal part of the delivering device. The directional element is adapted for directing optical radiation to the delivering device. The polarization-sensitive common path optical coherence reflectometer further includes optoelectronic selecting means optically coupled with the directional element. The optoelectronic selecting means includes optical means optically coupled with optoelectronic registering means. The optical means is adapted for splitting the combined optical radiation, incoming from the delivering device through the directional element, into at least two parts of the optical radiation propagating therethrough with a preset optical path length difference, and further recombining the at least two parts of the optical radiation.

The optoelectronic selecting means is adapted for selecting at least one of the following: a cross-polarized component of the combined optical radiation representative of an optical radiation having returned from an associated sample, and a parallel-polarized component of the combined optical radiation representative of an optical radiation having returned from an associated sample, subject to the preset optical path length difference for the at least two parts of the optical radiation propagating through the optical means.

According to yet another aspect of the subject application, there is provided a polarization sensitive common path optical coherence reflectometer including a source of optical radiation and converting means optically coupled with the source of optical radiation. The converting means is adapted for producing at least two cross-polarized replicas of the optical radiation incoming from the source of optical radiation and propagating therethrough with an optical path length difference. The reflectometer also includes a delivering device adapted for forming and delivering an optical radiation beam to an associated sample. The delivering device includes a proximal part and a distal part, wherein the distal part of the delivering device includes a reference reflector. The delivering device is further adapted for producing a combined optical radiation representative of an optical radiation having returned from an associated sample, the combined optical radiation being a combination of an optical radiation having returned from an associated sample and of an optical radiation reflected from the reference reflector.

Further included in the polarization sensitive common path optical coherence reflectometer of the subject application, are directional splitting means and a directional element. The directional element is optically coupled with the converting means, with the proximal part of the delivering device, and with the directional splitting means. The directional element is adapted for directing optical radiation to the delivering device and is adapted for directing optical radiation to the directional splitting means. Further included in the reflectometer of the present invention, is first optoelectronic selecting means and second optoelectronic selecting means, each optically coupled with the directional splitting means. The directional splitting means is adapted for splitting the combined optical radiation, incoming from the directional element into two parts, directing one part of the combined optical radiation to the first optoelectronic selecting means, and directing another part of the combined optical radiation to the second optoelectronic selecting means.

The first optoelectronic selecting means includes first optical means optically coupled with first optoelectronic registering means. The second optoelectronic selecting means includes second optical means optically coupled with second optoelectronic registering means. The first optical means is adapted for splitting the combined optical radiation, incoming from the delivering device through the directional element and the directional splitting means, into at least two parts of the optical radiation propagating therethrough with a first preset optical path length difference, and further recombining the at least two parts of the optical radiation. The second optical means is adapted for splitting the combined optical radiation, incoming from the delivering device through the directional element and the directional splitting means, into at least two parts of the optical radiation propagating therethrough with a second preset optical path length difference, and further recombining the at least two parts of the optical radiation.

The first optoelectronic selecting means is adapted for selecting a cross-polarized component of the combined optical radiation representative of an optical radiation having returned from an associated sample. The second optoelectronic selecting means is adapted for selecting a parallel-polarized component of the combined optical radiation representative of an optical radiation having returned from an associated sample.

Thus, in accordance with the subject application, unlike previously known polarization sensitive common path OCT/OCR devices, optical radiation from a source is first converted into two cross-polarized replicas of the optical radiation propagating therethrough with a predetermined optical path length difference. The two cross-polarized replicas are then delivered to an associated sample by a delivering device, which is, preferably, an optical fiber probe. A combination optical radiation is produced in at least one secondary interferometer by combining an optical radiation returning from the associated sample with a reference optical radiation reflected from a tip of an optical fiber of the optical fiber probe. Subject to a preset optical path length difference of the arms of the at least one secondary interferometer, a cross-polarized component, and/or parallel-polarized component of the combined optical radiation, are selected. The topology of the devices allows for time domain, as well as for time frequency domain registration.

Still other objects and aspects of the present invention will become readily apparent to those skilled in this art from the following description wherein there are shown and described preferred embodiments of this invention, simply by way of illustration of the best modes suited for to carry out the invention. As it will be realized by those skilled in the art, the invention is capable of other different embodiments and its several details are capable of modifications in various obvious aspects all without departing from the scope of the subject application. Accordingly, the drawings and description will be regarded as illustrative in nature and not as restrictive.

BRIEF DESCRIPTION OF DRAWINGS

For a more complete understanding of the present invention and the advantages thereof, reference is now made to the following description taken in conjunction with the accompanying drawings, in which.

DETAILED DESCRIPTION OF THE INVENTION

The subject application is directed to systems and methods for visualizing subsurface regions of samples, and more specifically, to a polarization-sensitive common path optical coherence reflectometer and polarization-sensitive optical coherence tomography device that provide internal depth profiles and depth images of samples. Modifications of the polarization-sensitive common path optical coherence reflectometer are illustrated by means of examples of optical fiber devices being part of an apparatus for optical coherence tomography, although it is evident that they may be implemented with the use of bulk optic elements, and may be used as independent devices. The optical fiber implementation is preferable for use in medical applications, especially in endoscopy, where flexibility of the optical fiber provides convenient access to different tissues and organs, including internal organs via an endoscope.

Figure 1:
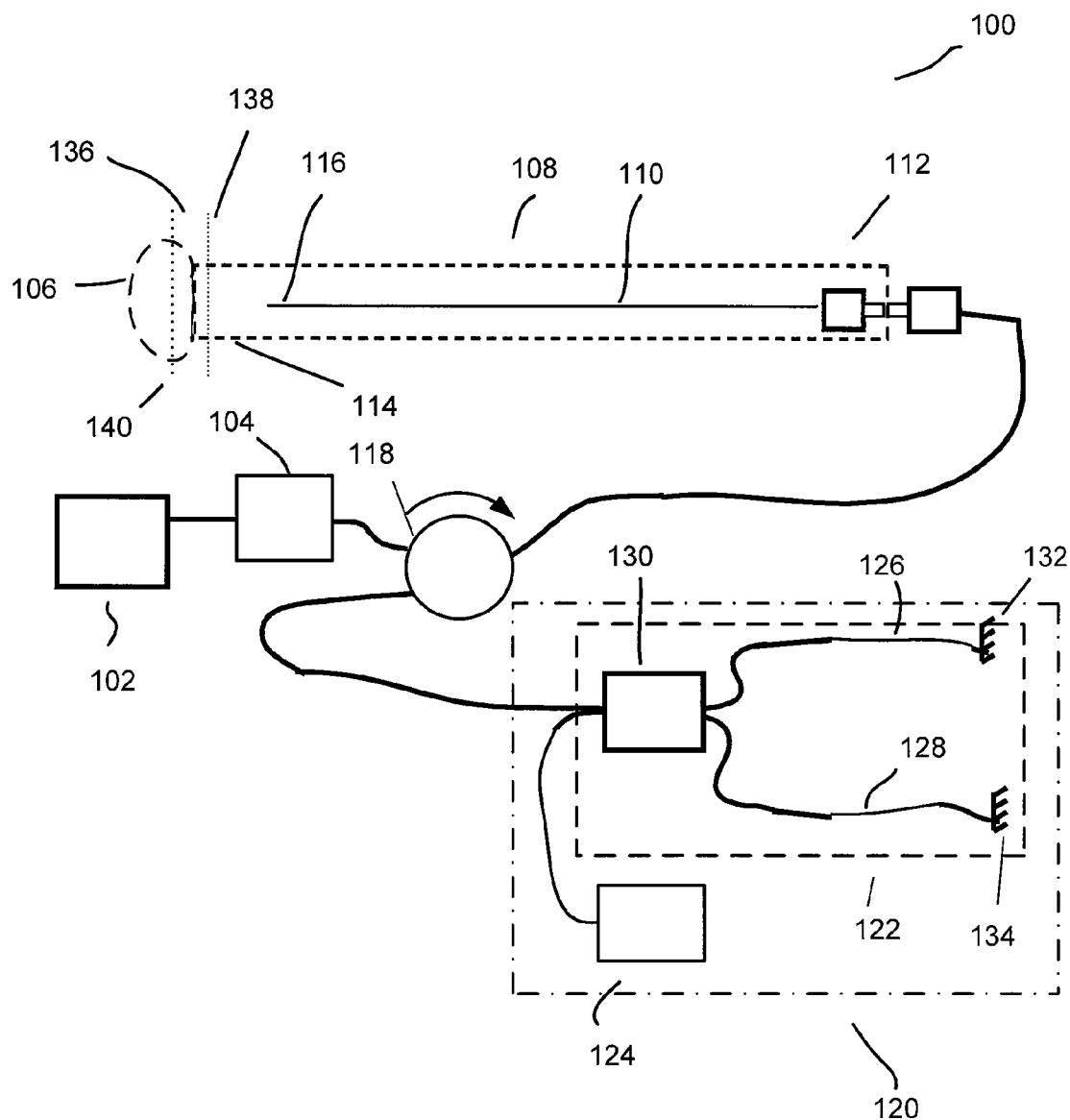
FIG. 1 is a block diagram of one preferred embodiment of the polarization-sensitive common path optical coherence reflectometer in accordance with the subject application.

Turning now to FIG. 1, there is shown a block diagram of a preferred embodiment of a polarization-sensitive common path optical coherence reflectometer 100, in accordance with the subject application. As shown in FIG. 1, the reflectometer 100 includes a source 102 of optical radiation, and converting means 104 optically coupled with the source 102 of optical radiation. In a preferred embodiment, the source 102 operates in the visible or near IR range. A skilled artisan will appreciate that the source 102 is, for example, and without limitation, a semiconductor superluminescent diode, solid state and fiberoptic femtosecond laser, and the like. The converting means 104 is adapted for producing at least two cross-polarized replicas of the optical radiation incoming from the source 102 of optical radiation, propagating therethrough with a predetermined optical path length difference. Those skilled in the art will appreciate that the converting means 104 is capable of several suitable implementations, examples of which will be described in greater detail below with reference to FIG. 3, FIG. 4, and FIG. 5.

The polarization-sensitive common path optical coherence reflectometer 100 further includes a delivering device adapted for forming and delivering an optical radiation beam to an associated sample 106. In the embodiment of FIG. 1, the delivering device is implemented as an optical fiber probe 108 that includes an optical fiber 110 extending therethrough. The optical fiber probe 108 includes a proximal part 112 and a distal part 114. The distal part 114 of the optical fiber probe 108 includes a reference reflector. In the embodiment of FIG. 1, a tip 116 of the optical fiber 110 placed in the distal part 114 of the optical fiber probe 108 is adapted for performing a function of the reference reflector. However, it will be evident to a skilled artisan that the delivering device as a whole, as well as the reference reflector being part to the delivering device, are capable of any other suitable implementations known in the art.

The optical fiber probe 108 is further adapted for producing a combined optical radiation representative of an optical radiation having returned from an associated sample 106. Those skilled in the art will appreciate that the combined optical radiation is a combination of an optical radiation having returned from an associated sample 106 and of an optical radiation reflected from the tip 116 of the optical fiber 110.

Further included in the reflectometer 100, as shown in FIG. 1, is a directional element 118 optically coupled with the converting means 104 and optically coupled with the proximal part 112 of the optical fiber probe 108. The directional element 118 is adapted for directing optical radiation to the optical fiber probe 108. A skilled artisan will appreciate that directional element 118 is capable of being implemented as any suitable directional element known in the art, such as, for example and without limitation, a suitable circulator or directional coupler. The polarization-sensitive common path optical coherence reflectometer 100 further includes optoelectronic selecting means 120 optically coupled with the directional element 118. The optoelectronic selecting means 120 includes optical means 122 optically coupled with optoelectronic registering means 124. In the embodiment illustrated in FIG. 1, the optical means 122 is adapted for splitting the combined optical radiation, incoming from the optical fiber probe 108 through the directional element 118, into two parts of the optical radiation propagating therethrough with a preset optical path length difference, and further recombining the two parts of the optical radiation.

In the embodiment shown in FIG. 1, the optical means 122 includes an optical path 126, an optical path 128, and a polarization insensitive element 130 adapted for splitting the combined optical radiation, incoming from the optical fiber probe 108 through the directional element 118, into two parts of the optical radiation and thereafter recombining the two parts of the optical radiation having propagated along respective optical paths 126, 128 in a forward and backward direction. Those skilled in the art will appreciate that the polarization insensitive element 130 is capable of any suitable implementation known in the art, such as, for example and without limitation, a 3 dB directional coupler. The optical paths 126, 128 in the optical means 122 include a Faraday mirror 132, 134, respectively, at their ends. The optical paths 126, 128 have a preset optical path length difference for the two parts of the optical radiation. As will be recognized by those skilled in the art, the optical means 122 is suitably capable of being implemented, for example and without limitation, as a suitable Michelson interferometer, as illustrated in FIG. 1, the optical paths 126, 128 being the arms of the Michelson interferometer. The optical paths 126, 128 are capable of including suitable delay elements, for example and without limitation, PZT delay elements (not shown in the drawing).

The optoelectronic selecting means 120 is adapted for selecting at least one of the following: a cross-polarized component of the combined optical radiation representative of an optical radiation having returned from an associated sample, and a parallel-polarized component of the combined optical radiation representative of an optical radiation having returned from an associated sample, subject to the preset optical path length difference for the at least two parts of the optical radiation propagating through the optical means 122.

As will be explained in greater detail below, the optoelectronic registering means 124 is capable of being implemented as time domain optoelectronic registering means including a data processing and displaying unit (not shown in FIG. 1). In this embodiment, the optical means 122 includes means adapted for changing the optical path length difference for the two parts of the optical radiation (not shown in FIG. 1). The optoelectronic registering means 124 is also capable of being implemented as a frequency domain optoelectronic registering means. Those skilled in the art will appreciate, that when the optoelectronic registering means 124 is a frequency domain optoelectronic registering means, the source 102 of optical radiation is capable of being narrowband and tunable, whereas the frequency domain optoelectronic registering means 124 includes at least one photodetector connected with a processing and displaying unit (not shown in FIG. 1). In another embodiment, the source 102 is broadband and implemented as a low-coherence source of optical radiation. In this embodiment, a spectrometer instead of a single photodiode is used in the frequency domain optoelectronic registering means 124, therefore parallel registration is performed instead of sequential.

A slow delay line suitably adapted to control the axial position of the observation zone is capable of being introduced in any of the arms of the optical means 122 (not shown in FIG. 1).

As will be recognized by those skilled in the art, the reflectometer 100 of the subject application is specified by a longitudinal range of interest 136 at least partially overlapping with an associated sample 106. The longitudinal range of interest 136 has a proximal boundary 138 and a distal boundary 140. The reflectometer 100 of the subject application is still further specified by an optical path length difference of a first value for an optical radiation beam propagating to the reference reflector (the tip 116 of the optical fiber 110) and to the proximal boundary 138 of the longitudinal range of interest 136. The reflectometer 100 of the subject application is yet further specified by an optical path length difference of a second value for the optical radiation beam propagating to the reference reflector (the tip 116 of the optical fiber 110) and to the distal boundary 140 of a longitudinal range of interest 136. The reflectometer 100 is further specified by an optical path length difference of a third value for the replicas of the optical radiation propagating through the converting means 104.

Preferably, a regular single mode optical fiber is used in the embodiment of the reflectometer of subject application, as depicted in FIG. 1.

Figure 2:
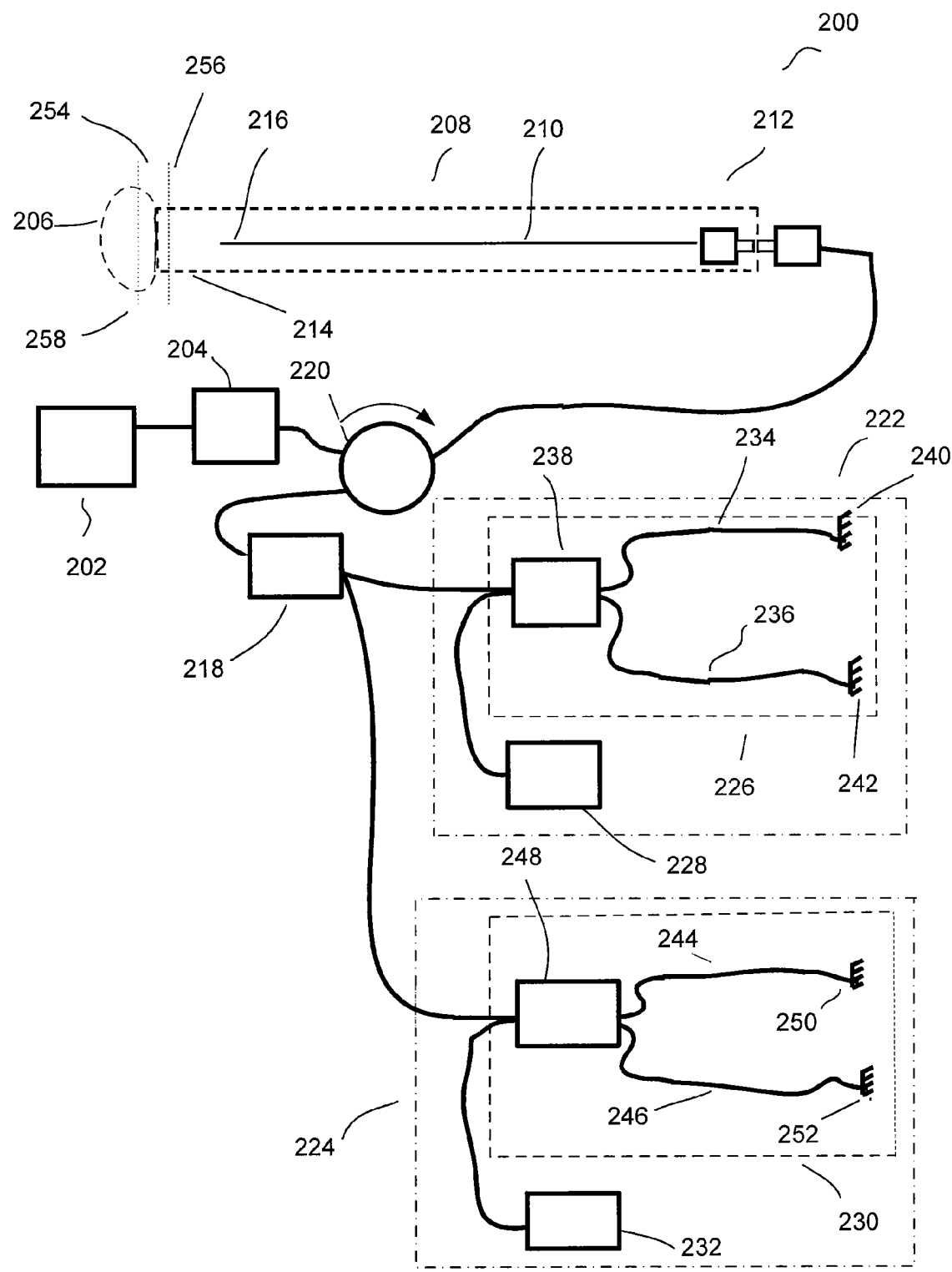
FIG. 2 is a block diagram of another preferred embodiment of the polarization-sensitive common path optical coherence reflectometer in accordance with the subject application.

Turning now to FIG. 2, there is shown a block diagram of another preferred embodiment of the polarization-sensitive common path optical coherence reflectometer 200, in accordance with the subject application. As shown in FIG. 2, the reflectometer 200 includes a source 202 of optical radiation, and converting means 204 optically coupled with the source 202 of optical radiation. The converting means 204 is adapted for producing at least two cross-polarized replicas of the optical radiation incoming from the source 202 of optical radiation and propagating therethrough with an optical path length difference. The reflectometer 200 also includes a delivering device adapted for forming and delivering an optical radiation beam to an associated sample 206. As will be recognized by a skilled artisan, the source 202, the converting means 204 and the delivering device are capable of being implemented analogous to respective elements referred to in the description of the embodiment shown in FIG. 1.

In the embodiment of FIG. 2, the delivering device is implemented as an optical fiber probe 208 that includes an optical fiber 210 extending therethrough. The optical fiber probe 208 includes a proximal part 212 and a distal part 214. The distal part 214 of the optical fiber probe 208 includes a reference reflector. In the embodiment of FIG. 2, a tip 216 of the optical fiber 210 placed in the distal part 214 of the optical fiber probe 208 is adapted for performing a function of the reference reflector. However, it will be evident to a skilled artisan that the delivering device as a whole, as well as the reference reflector being part to the delivering device, are capable of any other suitable implementations known in the art. The optical fiber probe 208 is further adapted for producing a combined optical radiation representative of an optical radiation having returned from an associated sample 206. Those skilled in the art will appreciate that the combined optical radiation is a combination of an optical radiation having returned from an associated sample 206 and of an optical radiation reflected from the tip 216 of the optical fiber 210.

Further included in the reflectometer 200, as shown in FIG. 2 are directional splitting means 218 and a directional element 220. The directional element 220 is optically coupled with the converting means 204, with the proximal part 212 of the optical fiber probe 208, and with the directional splitting means 218. As will be evident to one of ordinary skill in the art, the directional element 220 is capable of being implemented analogous to the directional element 118 of the embodiment illustrated in FIG. 1. Those skilled in the art will further recognize that directional splitting means 218 is, preferably, implemented as a 3 dB directional coupler. The directional element 220 is adapted for directing optical radiation to the optical fiber probe 208 and is adapted for directing optical radiation to the directional splitting means 218. Further included in the reflectometer 200 as illustrated in FIG. 2, is first optoelectronic selecting means recognize that the 222 and second optoelectronic selecting means 224, each optically coupled with the directional splitting means 218. The directional splitting means 218 is adapted for splitting the combined optical radiation, incoming from the directional element 220 into two fractions, directing one fraction of the combined optical radiation to the first optoelectronic selecting means 222, and directing another fraction of the combined optical radiation to the second optoelectronic selecting means 224.

The first optoelectronic selecting means 222 includes first optical means 226 optically coupled with first optoelectronic registering means 228. The second optoelectronic selecting means 224 includes second optical means 230 optically coupled with second optoelectronic registering means 232. In the embodiment illustrated in FIG. 2, the first optical means 226 is adapted for splitting the fraction of combined optical radiation, incoming from the optical fiber probe 208 through the directional element 220 and the directional splitting means 218, into two parts of the optical radiation propagating therethrough with a first preset optical path length difference, and further recombining the two parts of the optical radiation. The second optical means 230 is adapted for splitting the fraction of combined optical radiation, incoming from the optical fiber probe 208 through the directional element 220 and the directional splitting means 218, into two parts of the optical radiation propagating therethrough with a second preset optical path length difference, and further recombining the two parts of the optical radiation.

Those of ordinary skill in the art will recognize that in the embodiment of FIG. 2, the first and second optical means 226, 230 are capable of being implemented analogous to the optical means 122 of the embodiment shown in FIG. 1. As illustrated in FIG. 2, the first optical means 226 includes optical paths 234, 236 and a polarization insensitive element 238. The polarization insensitive element 238 is adapted for splitting the fraction of combined optical radiation, incoming from the optical fiber probe 208 through the directional element 220 and the directional splitting means 218, into two parts of the optical radiation and thereafter recombining the two parts of the optical radiation having propagated along respective optical paths 234, 236 in a forward and backward direction. Each optical path 234, 236, includes a respective Faraday mirror 240, 242, at its end. The two optical paths 234, 236 s in the first optical means 226, 230 have a first preset optical path length difference for the two parts of the optical radiation.

The second optical means 230, as shown in FIG. 2, includes optical paths 244, 246 and a polarization insensitive element 248. The polarization insensitive element 248 is adapted for splitting the fraction of combined optical radiation, incoming from the optical fiber probe 208 through the directional element 220 and the directional splitting means 218, into two parts of the optical radiation and thereafter recombining the two parts of the optical radiation having propagated along respective optical paths 244, 246 in a forward and backward direction. Each optical path 244, 246, includes a respective Faraday mirror 250, 252, at its end. The two optical paths 244, 246 in the second optical means 226, 230 have a second preset optical path length difference for the two parts of the optical radiation.

The first optoelectronic selecting means 222 is adapted for selecting a cross-polarized component of the combined optical radiation representative of an optical radiation having returned from an associated sample 206. The second optoelectronic selecting means 224 is adapted for selecting a parallel-polarized component of the combined optical radiation representative of an optical radiation having returned from an associated sample 206.

The optoelectronic registering means 228, 232 are capable of being implemented analogous to the optoelectronic registering means 124, as described above with respect to the embodiment of FIG. 1. The optoelectronic registering means 228, 232 are capable of being implemented as time domain optoelectronic registering means including a data processing and displaying unit (not shown in FIG. 2). When this implementation is used, the first and second optical means 226, 230, respectively, each include respective means adapted for changing the optical path length difference for the two respective parts of the optical radiation. The optoelectronic registering means 228, 232 are also capable of being implemented as frequency domain optoelectronic registering means.

A slow delay line suitably adapted to control the axial position of the observation zone is capable of being introduced in any of the arms of optical means 224, 226 (not shown in FIG. 2).

As will be recognized by those skilled in the art, the reflectometer 200 of the subject application is specified by a longitudinal range of interest 254 at least partially overlapping with an associated sample 206. The longitudinal range of interest 254 has a proximal boundary 256 and a distal boundary 258.

Figure 3:
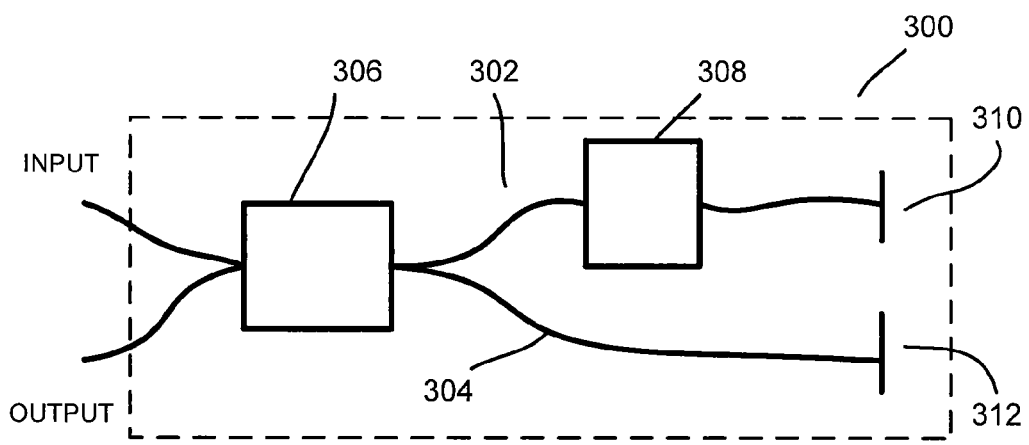
FIG. 3 is a block diagram of one preferred embodiment of the converting means in accordance with the subject application.

Turning now to FIG. 3, there is shown a block diagram of one preferred embodiment of converting means 300, which represents converting means 104 and converting means 204, with respect to FIGS. 1, 2, respectively, in accordance with the subject application. As shown in FIG. 3, the converting means 300 includes optical paths 302, 304 and an element 306 adapted for splitting the optical radiation, incoming from the source of optical radiation, which is 102 in FIG. 1, and 202 in FIG. 2, into two replicas of the optical radiation and thereafter recombining the two replicas of the optical radiation having propagated along respective optical paths 302, 304 in a forward and backward direction. The optical paths 302, 304 include each a mirror at their ends. As shown in FIG. 3, the optical path 304 includes a polarization controller 308 adapted for controlling the polarization state of an associated replica of the optical radiation such, so as to convert the initial polarization state of the associated replica to an orthogonal polarization state with respect to the initial polarization state. Those skilled in the art will appreciate that a polarization controller is capable of being included in each optical path 302, 304. That being the case, a polarization state of each associated replica is not necessarily converted to an orthogonal one with respect to the initial polarization state. However, the polarization controllers control the polarization states of associated replicas of the optical radiation such, that the two replicas returning to the element 306 are cross-polarized replicas of the optical radiation.

The optical paths 302, 304 include regular mirrors 310, 312, respectively, at their ends, and have a predetermined optical path length difference for the two replicas of the optical radiation. As will be recognized by those skilled in the art, the converting means 300, as illustrated in FIG. 3, is a suitable Michelson interferometer, the optical paths 302, 304 being the arms of the Michelson interferometer. A skilled artisan will appreciate that the input of the converting means 300 is optically coupled with the source of optical radiation (102 in FIG. 1; 202 in FIG. 2) and the output is optically coupled with a respective input of the directional element (118 in FIG. 1; 220 in FIG. 2). The element 306 is preferably implemented as a suitable 3 dB coupler. The optical paths 302, 304 are capable of including suitable delay elements, for example and without limitation, PZT delay elements (not shown in the drawing). The PZT delay elements are optional, since the interferometer is capable of being made with a factory fixed predetermined optical path length difference in the interferometer arms, though one or two PZT delay elements may be used for precise tuning.

Typically the elements of the converting means 300 and any elements located between the source of optical radiation (102 in FIG. 1; 202 in FIG. 2) and the converting means 300 are pre-packed in a way to allow for no bending or flexing during operation and maintenance of the reflectometer of the subject application. Hence the polarization controller 308 can be factory aligned to after all fiber optic packaging to ensure that the two replicas returning to the element 306 are cross-polarized mutually coherent replicas of the optical radiation.

Figure 4:
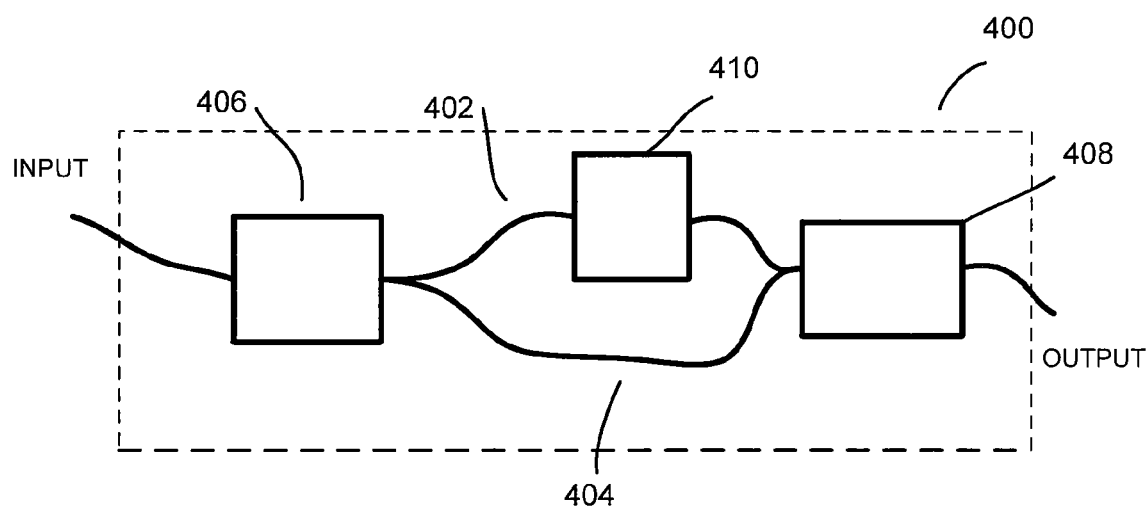
FIG. 4 is a block diagram of one preferred embodiment of the converting means in accordance with the subject application.

Turning now to FIG. 4, there is shown a block diagram of another preferred embodiment of converting means 400, which represents converting means 104 and converting means 204, with respect to FIGS. 1, 2, respectively, in accordance with the subject application. As shown in FIG. 4, the converting means 400 includes optical paths 402, 404 and an element 406 adapted for splitting the optical radiation, incoming from the source of optical radiation, which is 102 in FIG. 1, and 102 in FIG. 2, into two replicas of the optical radiation. In this embodiment, the converting means 400 further includes an element 408 adapted for recombining the two replicas of the optical radiation having propagated along respective optical paths 402, 404 in a forward direction. As shown in FIG. 4, the optical path 402 includes a polarization controller 410 adapted for controlling the polarization state of an associated replica of the optical radiation such, so as to convert the initial polarization state of the associated replica to an orthogonal polarization state with respect to the initial polarization state. Those skilled in the art will appreciate that a polarization controller is capable of being included in each optical path 402, 404. That being the case, a polarization state of each associated replica is not necessarily converted to an orthogonal one with respect to the initial polarization state. However, the polarization controllers control the polarization states of associated replicas of the optical radiation such, that the two replicas entering the element 406 are cross-polarized mutually coherent replicas of the optical radiation.

As will be recognized by those skilled in the art, the converting means 400, as illustrated in FIG. 4, is a suitable Mach-Zehnder interferometer, the optical paths 402, 404 being the arms of the Mach-Zehnder interferometer. The elements 406, 408 are preferably implemented as suitable 3 dB couplers. A skilled artisan will appreciate that the input of the converting means 400 is optically coupled with the source of optical radiation (102 in FIG. 1; 202 in FIG. 2) and the output is optically coupled with a respective input of the directional element (118 in FIG. 1; 220 in FIG. 2). The optical paths 402, 404 have a predetermined optical path length difference for the two replicas of the optical radiation. The optical paths 402, 404 are capable of including suitable delay elements, for example and without limitation, PZT delay elements (not shown in the drawings). The PZT delay elements are optional, since the interferometer the same as the interferometer depicted in FIG. 3, is capable of being made with a factory fixed predetermined optical path length difference in the interferometer arms, though one or two PZT delay elements may be used for precise tuning.

The elements of the converting means 400 and any elements located between the source of optical radiation (102 in FIG. 1; 202 in FIG. 2) and the converting means 400 are pre-packed in a way to allow for no bending or flexing during operation and maintenance of the reflectometer of the subject application. Hence the polarization controller 410 can be factory aligned to after all fiber optic packaging to ensure that the two replicas returning to the element 406 are cross-polarized replicas of the optical radiation.

Figure 5:
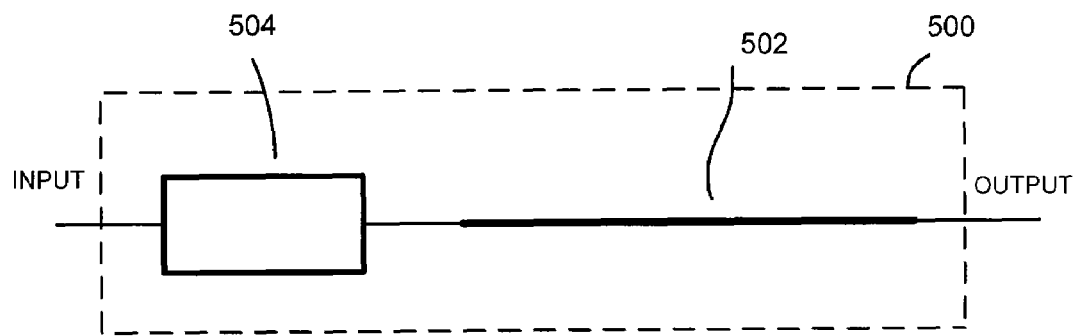
FIG. 5 is a block diagram of one preferred embodiment of the converting means in accordance with the subject application.

Turning now to FIG. 5, there is shown a block diagram of yet another preferred embodiment of converting means 500, which represents the converting means 104 and converting means 204, with respect to FIGS. 1, 2, respectively, in accordance with the subject application. As shown in FIG. 5, the converting means 500 includes a portion of polarization maintaining optical fiber 502 adapted for producing two cross-polarization modes of the optical radiation propagating therethrough with a predetermined optical path length difference. The converting means 500 further includes a polarization controller 504 placed at the input of the converting means 500. The polarization controller 504 is adapted for controlling a power ratio between the two cross-polarization modes of the optical radiation propagating through the portion of polarization maintaining optical fiber 502. As will be appreciated by those of ordinary skill in the art, the predetermined optical path length difference for the two cross-polarization modes of the optical radiation propagating therethrough is defined by the optical properties of the portion of polarization maintaining optical fiber 502.

Figure 6:
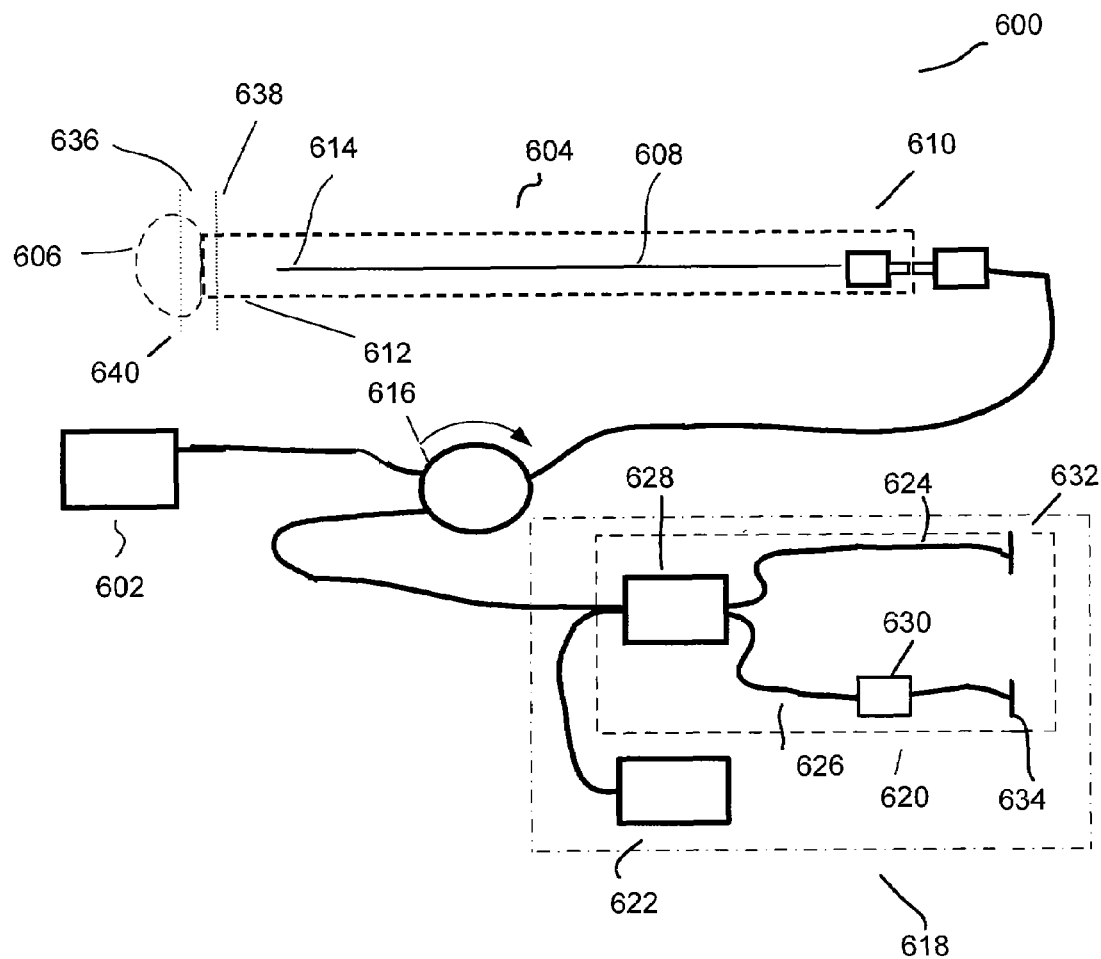
FIG. 6 is a block diagram of another preferred embodiment of the polarization-sensitive common path optical coherence reflectometer in accordance with the subject application.

Turning now to FIG. 6, there is shown a block diagram of another embodiment of the polarization-sensitive common path optical coherence reflectometer 600, in accordance with the subject application. As shown in FIG. 6, the reflectometer 600 includes a source 602 of optical radiation and a delivering device adapted for forming and delivering an optical radiation beam to an associated sample 606. In the embodiment of FIG. 6, the delivering device 604 is implemented as an optical fiber probe 604 that includes an optical fiber 608 extending therethrough. The optical fiber probe 604 includes a proximal part 610 and a distal part 612. The distal part 612 of the optical fiber probe 604 includes a reference reflector. In the embodiment of FIG. 6, a tip 614 of the optical fiber 608 placed in the distal part 612 of the optical fiber probe 604 is adapted for performing a function of the reference reflector. However, it will be evident to a skilled artisan that the delivering device as a whole, as well as the reference reflector being part to the delivering device, are capable of any other suitable implementations known in the art.

The optical fiber probe 604 is further adapted for producing a combined optical radiation representative of an optical radiation having returned from an associated sample 606. Those skilled in the art will appreciate that the combined optical radiation is a combination of a sample portion of the optical radiation having returned from an associated sample 606 and of a reference portion of the optical radiation reflected from the tip 614 of the optical fiber 608.

Also included in the reflectometer 600, as shown in FIG. 6, is a directional element 616 optically coupled with the source 602 of optical radiation and with the proximal part 610 of the optical fiber probe 604. The directional element 616 is adapted for directing optical radiation to the optical fiber probe 604. A skilled artisan will appreciate that directional element 616 is capable of being implemented as any suitable directional element known in the art. The polarization-sensitive common path optical coherence reflectometer 600 further includes optoelectronic selecting means 618 optically coupled with the directional element 616. The optoelectronic selecting means 618 includes converting means 620 optically coupled with optoelectronic registering means 622.

In the embodiment illustrated in FIG. 6, the converting means 620 is adapted for splitting the sample portion and the reference portion of the combined optical radiation incoming from the delivering device 604 through the directional element 616, into at least two parts propagating therethrough with a preset optical path length difference. The converting means 620 is also adapted for further recombining the at least two parts of the optical radiation. The converting means 620 is further adapted for converting the reference portion of at least one part of the optical radiation such that the reference portions of the at least two parts of the optical radiation are cross-polarized portions of optical radiation. The optoelectronic selecting means 618 is adapted for selecting a cross-polarized component of the combined optical radiation representative of an optical radiation having returned from an associated sample 606.

In the embodiment shown in FIG. 6, the converting means 620 includes an optical path 624, an optical path 626, and a polarization insensitive element 628 adapted for splitting the combined optical radiation, incoming from the delivering device 604 through the directional element 616, into two parts of the optical radiation and thereafter recombining the two parts of the optical radiation having propagated along respective optical paths 624, 626 in a forward and backward direction. The optical path 626 includes a polarization controller 630 adapted for controlling the polarization state of an associated portion of the optical radiation. The optical path 624 in the converting means 620 includes a mirror 632 at its end, which is capable of being implemented as a Faraday mirror, but, preferably, is a regular mirror, as shown in FIG. 6. The optical path 626 includes a regular mirror 634 at its end. The optical paths 624, 626 have a preset optical path length difference for the two parts of the optical radiation.

As will be explained in greater detail below, the optoelectronic registering means 622 is capable of being implemented as time domain optoelectronic registering means including a data processing and displaying unit (not shown in FIG. 6). In this embodiment, the optical means 620 includes means adapted for changing the optical path length difference for the two parts of the optical radiation (not shown in FIG. 6). The optoelectronic registering means 622 is also capable of being implemented as a frequency domain optoelectronic registering means. Those skilled in the art will appreciate, that when the optoelectronic registering means 622 is a frequency domain optoelectronic registering means, the source 602 of optical radiation is capable of being narrowband and tunable, whereas the frequency domain optoelectronic registering means 622 includes at least one photodetector connected with a processing and displaying unit (not shown in FIG. 6). In another embodiment the source 602 is broadband and implemented as a low-coherence source of optical radiation. In this embodiment a spectrometer instead of a single photodiode is used in the frequency domain optoelectronic registering means 622, therefore parallel registration is performed instead of sequential.

As will be recognized by those skilled in the art, the reflectometer 600 of the subject application is specified by a longitudinal range of interest 636 at least partially overlapping with an associated sample 606. The longitudinal range of interest 636 has a proximal boundary 638 and a distal boundary 640.

Figure 7:
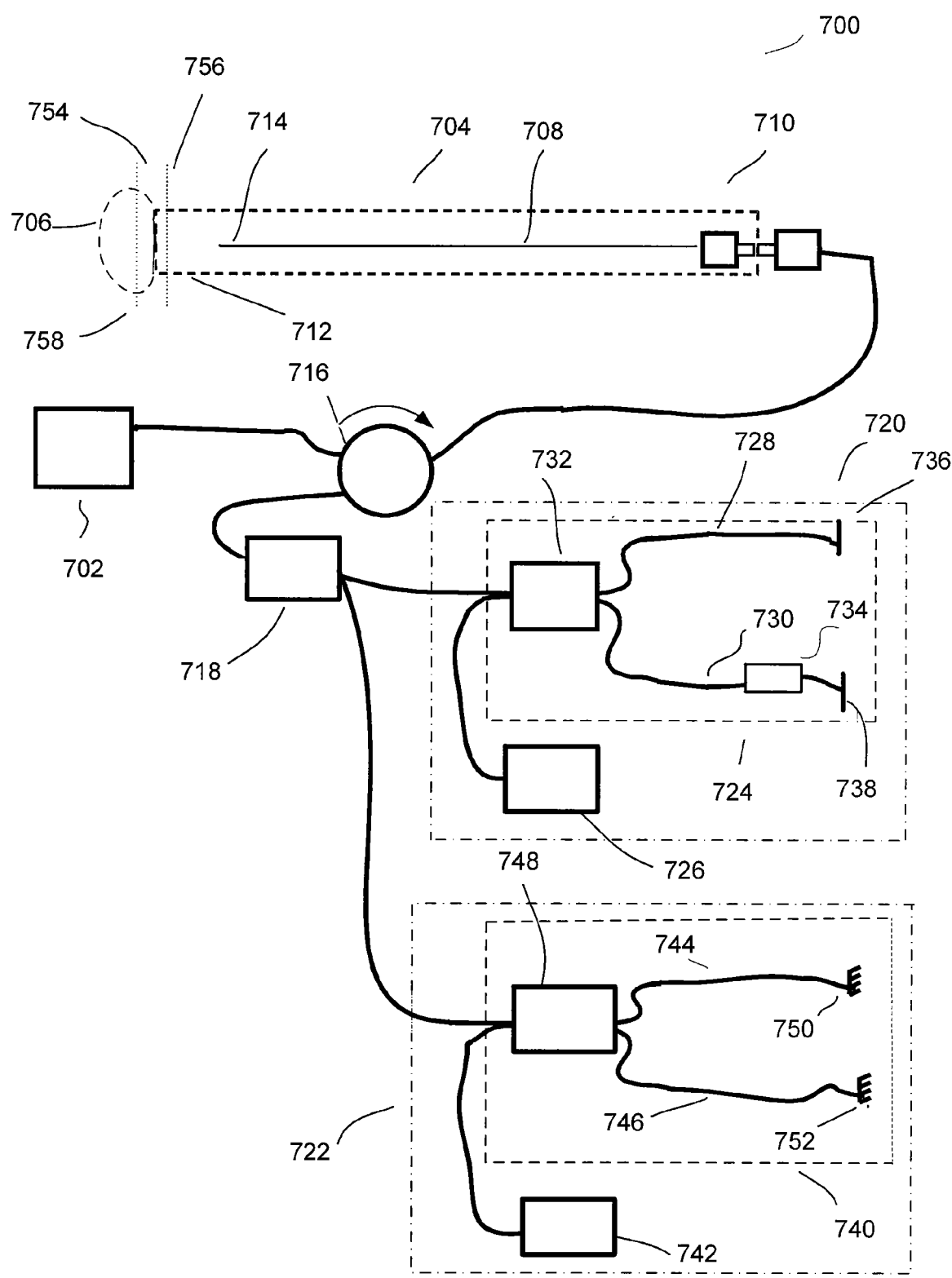
FIG. 7 is a block diagram of another preferred embodiment of the polarization-sensitive common path optical coherence reflectometer in accordance with the subject application.

Turning now to FIG. 7, there is shown a block diagram of another preferred embodiment of the polarization-sensitive common path optical coherence reflectometer 700, in accordance with the subject application. As shown in FIG. 7, the reflectometer 700 includes a source 702 of optical radiation and a delivering device adapted for forming and delivering an optical radiation beam to an associated sample 706. In the embodiment of FIG. 7, the delivering device is implemented as an optical fiber probe 704 that includes an optical fiber 708 extending therethrough. The optical fiber probe 704 includes a proximal part 710 and a distal part 712. The distal part 712 of the optical fiber probe 704 includes a reference reflector. In the embodiment of FIG. 7, a tip 714 of the optical fiber 708 placed in the distal part 712 of the optical fiber probe 704 is adapted for performing a function of the reference reflector. However, it will be evident to a skilled artisan that the delivering device as a whole, as well as the reference reflector being part to the delivering device, are capable of any other suitable implementations known in the art.

The optical fiber probe 704 is further adapted for producing a combined optical radiation representative of an optical radiation having returned from an associated sample 706. Those skilled in the art will appreciate that the combined optical radiation is a combination of an optical radiation having returned from an associated sample 706 and of an optical radiation reflected from the tip 714 of the optical fiber 708.

Also included in the reflectometer 700, as shown in FIG. 7, is a directional element 716 optically coupled with the source 702 of optical radiation and with the proximal part 710 of the delivering device 704. The directional element 716 is adapted for directing optical radiation to the delivering device 704. A skilled artisan will appreciate that directional element 716 is capable of being implemented as any suitable directional element known in the art. The polarization-sensitive common path optical coherence reflectometer 700 further includes directional splitting means 718, first optoelectronic selecting means 720, and second optoelectronic selecting means 722. The first optoelectronic selecting means 720 and second optoelectronic selecting means 722 are each optically coupled with the directional splitting means 718. The directional splitting means 718 is adapted for splitting the combined optical radiation, incoming from the directional element 716 into two fractions, directing one fraction of the combined optical radiation to the first optoelectronic selecting means 720, and directing another fraction of the combined optical radiation to the second optoelectronic selecting means 722.

The first optoelectronic selecting means 720 includes converting means 724 optically coupled with first optoelectronic registering means 726. In the embodiment illustrated in FIG. 7, the converting means 724 is adapted for splitting the sample portion and the reference portion of the fraction of the combined optical radiation incoming from the delivering device 704 through the directional element 716, into at least two parts propagating therethrough with a preset optical path length difference. The converting means 720 is also adapted for further recombining the at least two parts of the optical radiation. The converting means 720 is further adapted for converting the reference portion of at least one part of the optical radiation such that the reference portions of the at least two parts of the optical radiation are cross-polarized portions of optical radiation. The first optoelectronic selecting means 720 is adapted for selecting a cross-polarized component of the combined optical radiation representative of an optical radiation having returned from an associated sample 706.

In the embodiment shown in FIG. 7, the converting means 724 includes an optical path 728, an optical path 730, and a polarization insensitive element 732 adapted for splitting the fraction of the combined optical radiation, incoming from the optical fiber probe 704 through the directional element 716 and the directional splitting means 718, into two parts of the optical radiation and thereafter recombining the two parts of the optical radiation having propagated along respective optical paths 728, 730 in a forward and backward direction. The optical path 730 includes a polarization controller 734 adapted for controlling the polarization state of an associated portion of the optical radiation. The optical path 728 in the converting means 720 includes a mirror 736 at its end, which is capable of being implemented as a Faraday mirror, but, preferably, is a regular mirror, as shown in FIG. 7. The optical path 730 includes a regular mirror 738 at its end. The optical paths 728, 730 have a first preset optical path length difference for the two parts of the optical radiation.

The first optoelectronic selecting means 720 is adapted for selecting a cross-polarized component of the combined optical radiation representative of an optical radiation having returned from an associated sample 706. As will be appreciated by those of ordinary skill in the art, the first optoelectronic selecting means 720 is capable of being implemented analogous to the optoelectronic selecting means 618, as described above with respect to the embodiment of FIG. 6.

The second optoelectronic selecting means 722 is adapted for selecting a parallel-polarized component of the combined optical radiation representative of an optical radiation having returned from an associated sample 706. The second optoelectronic selecting means 722 includes optical means 740 optically coupled with second optoelectronic registering means 742. In the embodiment illustrated in FIG. 7, the optical means 740 is adapted for splitting the fraction of combined optical radiation, incoming from the optical fiber probe 704 through the directional element 716 and directional splitting means 718, into two parts of the optical radiation propagating therethrough with a second preset optical path length difference, and further recombining the two parts of the optical radiation.

Those of ordinary skill in the art will recognize, that in the embodiment of FIG. 7, the optical means 740 is capable of being implemented analogous to the second optical means 224 of the embodiment shown in FIG. 2. As illustrated in FIG. 7, the optical means 740 includes optical paths 744, 746 and a polarization insensitive element 748. The polarization insensitive element 748 is adapted for splitting the part of combined optical radiation, incoming from the delivering device 704 through the directional element 716 and the directional splitting means 718, into two replicas of the optical radiation and thereafter recombining the two replicas of the optical radiation having propagated along respective optical paths 744, 746 in a forward and backward direction. Each optical path 744, 746, includes a respective Faraday mirror 750, 752, at its end. The two optical paths 744, 746 in the optical means 740 have a second preset optical path length difference for the respective two parts of the optical radiation.

The optoelectronic registering means 726, 742 are capable of being implemented analogous to the optoelectronic registering means 228, 232, as described in detail above with respect to the embodiment of FIG. 2.

As will be recognized by those skilled in the art, the reflectometer 700 of the subject application is specified by a longitudinal range of interest 754 at least partially overlapping with an associated sample 706. The longitudinal range of interest 754 has a proximal boundary 756 and a distal boundary 758.

In accordance with another aspect of the invention, the embodiments of FIG. 1, FIG. 2, FIG. 6, and FIG. 7 are capable of further including means for changing relative positions of the optical radiation beam being delivered to an associated sample, and the associated sample (not shown in the drawing). In these embodiments, the polarization sensitive common path reflectometers illustrated in FIGS. 1, 2, 6, and 7, each are part of a polarization sensitive common path device for optical coherence tomography. Those of ordinary skill in the art will recognize, that in these devices, the means for changing relative positions of the optical radiation beam being delivered to the associated sample, and the associated sample is suitably capable of being implemented in any way known in the art, for example and without limitation, as a lateral scanner incorporated into the delivering device, or as an element for changing the position of an associated sample.

Referring now to operation of the polarization sensitive common path optical coherence reflectometer 100 in accordance with the present invention shown in FIG. 1, the operation of the reflectometer 100 commences by placing the delivering device, preferably implemented as an optical fiber probe 108, at a predetermined position with respect to an associated sample 106. Depending basically on the tasks performed, the optical fiber probe 108 is placed in the vicinity of an associated sample 106, in contact with an associated sample 106, or at a predetermined distance from an associated sample 106. In all cases, as previously mentioned, there exists a distance between the tip 116 of the optical fiber 110, the tip 116 serving as a reference reflector, and the proximal boundary 138 of the longitudinal range of interest 136, which will be referred to hereinafter as an optical path length of a first value (reference offset). The distance between the tip 116 of the optical fiber 110 and the distal boundary 140 of the longitudinal range of interest 136, will be referred to hereinafter as an optical path length of a second value. Hence, in the preferred embodiment the tip 116 of the optical fiber 110 is positioned at a distance having a first optical length value from the proximal boundary 138 of the longitudinal range of interest 136 (reference offset), or, in other words, having a second optical length value from the distal boundary 140 of the longitudinal range of interest 136.

Next, an optical radiation from the source 102 is directed to the converting means 104. The source 102 of optical radiation is capable of being implemented as a source of polarized or partially polarized optical radiation. In the latter case, the polarized part of the optical radiation coming from the source 102 is used. Those skilled in the art will appreciate that when the source 102 is implemented as a source of non-polarized optical radiation, a polarizer is suitably included therein coupled with the output of source (not shown in the drawing). For the sake of simplicity the following description is made for a polarized optical radiation outgoing from the source 102.

As mentioned above, the converting means 104 is adapted for producing two cross-polarized replicas of the polarized optical radiation incoming from the source 102 of optical radiation, propagating therethrough with a predetermined optical path length difference, which will be referred to hereinafter as an optical path length of a third value. Reference will be now made to FIG. 3 illustrating converting means 300, which represents an embodiment of converting means 104 in FIG. 1. The polarized optical radiation entering the converting means 300 is split into two, preferably, identical replicas of the optical radiation by the element 306. One replica propagates along the optical path 304 and after being reflected by the regular mirror 312 returns to the element 306. The other replica, which propagates along the optical path 302, passes through the polarization controller 308 in a forward direction and after being reflected by the regular mirror 310 passes through the polarization controller 308 in a backward direction, thus returning to the element 306. As will be appreciated by those skilled in the art, the polarization controller 308 converts the polarization state of the replica propagating along the optical path 302 such, that the two replicas are cross-polarized as they enter the element 306. The element 306 suitably recombines the two replicas after they have propagated along respective optical paths 302, 304 with a predetermined optical path difference in a forward and backward direction.

As will be recognized by those skilled in the art, when the converting means 300 implemented as a Michelson interferometer is used in the embodiment of FIG. 1, an additional directional element or isolator may be needed between the source of optical radiation 102 and the converting means 104 to prevent the back reflection and appropriate source reaction (not shown in the drawing).

Reference will be now made to FIG. 4 illustrating converting means 400, which represents another embodiment of the converting means 104 in FIG. 1. The polarized optical radiation entering the converting means 400 is split into two, preferably, identical replicas of the optical radiation by the element 406. One replica propagates along the path 404 in a forward direction and enters the element 408. The other replica that propagates along the path 402 in a forward direction passes through the polarization controller 410. As will be appreciated by those skilled in the art, the polarization controller 410 converts the polarization state of the replica propagating along the optical path 402 such, that the two replicas are cross-polarized as they enter the element 408. The element 408 suitably recombines the two replicas after they have propagated along respective optical paths 402, 404 with a predetermined optical path difference in a forward direction.

Reference will be now made to FIG. 5 illustrating converting means 500, which represents yet another embodiment of the converting means 104 in FIG. 1. The polarized optical radiation from the source 102 enters the converting means 400. The polarization maintaining optical fiber 502 produces two eigen modes of the optical radiation propagating therethrough, which are cross-polarization modes of the optical radiation. As will be appreciated by a skilled artisan, the cross-polarization modes of the optical radiation experience a predetermined optical path length difference, which is defined by the optical properties of the polarization maintaining optical fiber 502. This optical path length difference is capable of being suitably chosen in the process of manufacturing and assembling by selecting the appropriate type and length of the polarization maintaining optical fiber 502. A typical length range for the polarization maintaining optical fiber 502 is capable of being from several meters to several tens of meters. The polarization controller 504 controls a power ratio between the two cross-polarization modes of the optical radiation propagating through the portion of polarization maintaining optical fiber 502, and, hence between the two replicas of the optical radiation. Typically, a ratio of 1:1 is considered desirable.

Thus, turning back to FIG. 1, outgoing from the converting means 104 are two cross-polarized replicas of the optical radiation propagating with a predetermined optical path length difference. In the embodiment illustrated in FIG. 1, the two replicas enter the optical fiber probe 108 through the directional element 118. The optical fiber probe 108 is adapted for forming and delivering an optical radiation beam to an associated sample 106. Thus, one part of the optical radiation beam corresponding to each replica is delivered to an associated sample 106 and is reflected or backscattered from it (the sample portion). Assuming the optical properties of an associated sample 106 such that they have an influence on the polarization state of the incident optical radiation, the optical radiation reflected or backscattered from an associated sample 106 corresponding to each replica, has a polarization state which differs from that of the incident optical radiation. As will be recognized by those skilled in the art, the optical radiation reflected or backscattered from an associated sample 106, corresponding to each replica, includes a superposition of two mutually coherent orthogonal components. It will be also apparent to those skilled in the art that of the two mentioned mutually coherent orthogonal components, one is parallel-polarized with respect to the polarization state of the incident sample portion, whereas the other component is cross-polarized with respect to the incident sample portion. The magnitudes of the components are subject to the depolarization influence of an associated sample 106.

Another part of the optical radiation beam corresponding to each replica of the optical radiation that enters the optical fiber probe 108 does not reach an associated sample 106, but is instead reflected at the tip 116 of the optical fiber 110 of the optical fiber probe 108, at some distance from an associated sample 106 (the reference portion). Obviously, the optical properties of an associated sample 106 have no influence on the polarization state of the reference portion of the optical radiation. Thus, the polarization state of the reference portion corresponding to each replica will remain the same as that of the incident optical radiation.

The optical radiation returning from the optical fiber probe 108 is a combination of the reference portion and the reflected or backscattered sample portion, corresponding to both replicas, shifted axially. The polarization state relationship between respective portions of optical radiation corresponding to the two replicas, does not change as the replicas propagate through the optical fiber probe 108, since all portions of the optical radiation propagate through the same optical path. This combined optical radiation is directed through the directional element 118 to the optical means 122, which is part to the optoelectronic selecting means 120. The directional element 118, the same as the optical fiber probe 108, has no influence on the polarization state relationship between respective portions of optical radiation corresponding to the two replicas.

The element 130 of the optical means 122 splits the combined optical radiation, incoming from the optical fiber probe 108 through the directional element 118, into two parts of the optical radiation. In other words, the sample portion of the optical radiation incoming from the optical fiber probe 108, corresponding to each replica, is split into two parts by the element 130, and the reference portion of the optical radiation incoming from the optical fiber probe 108, corresponding to each replica, is split into two parts by the element 130. As mentioned previously, in the optical means 122, which in the embodiment depicted in FIG. 1 is implemented as a Michelson optical interferometer, a regular single mode optical fiber is used, which does not maintain the initial polarization state of the optical radiation. Hence, a random polarization change occurs in the optical paths 126, 128 for all portions of the optical radiation. However, the random polarization change for all portions of the optical radiation is completely compensated after the portions of the optical radiation are reflected from respective Faraday mirrors 132, 134, which provide a 90 degree polarization rotation for any incident optical radiation. That means that the reference and sample portions of optical radiation when returning to the element 130 from the optical paths 126, 128 will continue to have the same polarization state relationship as they had, entering the element 130 from the directional element 118.

The optoelectronic selecting means 120 is adapted for selecting a cross-polarized component, parallel-polarized component, or both components of the combined optical radiation representative of an optical radiation having returned from an associated sample 106. The selection is subject to the preset optical path length difference for the two parts of the optical radiation propagating through the optical means 120 along respective optical paths 126, 128. Also, depending on the value of the preset optical path length difference for the parts of the optical radiation propagating along respective optical paths 126, 128, frequency domain or time domain registration is capable of being provided. Those skilled in the art will appreciated that optical radiations having parallel polarizations interfere and those having orthogonal polarizations do not interfere. Hence, as will be explained in greater detail below with reference to FIGS. 8a, 8b and 8c and FIGS. 9a, 9b and 9c, the reference portion of one replica will interfere with a corresponding component of the sample portion of the other replica, and visa versa. As will be appreciated by those skilled in the art, an interference signal is then detected and processed in the same manner as in previously known OCR/OCT devices.

As mentioned above, the reflectometer 100 of the subject application is specified by an optical path length difference of a first value for an optical radiation beam propagating to the reference reflector (the tip 116 of the optical fiber 110) and to the proximal boundary 138 of the longitudinal range of interest 136. The reflectometer 100 is further specified by an optical path length difference of a second value for the optical radiation beam propagating to the reference reflector (the tip 116 of the optical fiber 110) and to the distal boundary 140 of a longitudinal range of interest 136. The reflectometer 100 is further specified by an optical path length difference of a third value for the replicas of the optical radiation propagating through the converting means 104.

Thus, in an embodiment with the value of the optical path length difference for the two parts of the optical radiation propagating through the optical means 122 selected from the group consisting of: substantially equal to the sum of the first value and the third value, and substantially equal to the difference between the first value and the third value, a cross-polarized component of the combined optical radiation representative of an optical radiation is having returned from an associated sample 106 is selected, using time domain registration. In this embodiment, the optical means 122 includes means adapted for changing the optical path length difference for the two parts of the optical radiation (not shown in the drawing). By scanning the optical path length difference of the optical paths 126, 128, the time profile of the combined optical radiation is obtained. Those skilled in the art will recognize that the scanning range is substantially equal to the longitudinal range of interest 136. As will be further appreciated by those skilled in the art, this time profile represents the in-depth profile of the reflected sample portion that is depolarized by an associated sample 106, of the optical radiation. For example and without limitation, a PZT fiber delay element is capable of being used for scanning the optical path length difference, which can be inserted in one or both interferometer arms (optical means 122). The obtained combined signal is equivalent to the interference signal from an "orthogonal" registration channel in previously known polarization sensitive OCT devices. In other words, a combination optical radiation, responsive to a portion of the reflected or backscattered optical radiation that is depolarized by the associated sample 106, is registered. As will be appreciated by a skilled artisan, the non-depolarized portion of the optical radiation reflected or backscattered from the associated sample 106 does not produce interference fringes and is not registered.

For selecting a parallel-polarized component of the combined optical radiation representative of an optical radiation having returned from an associated sample 106 using time domain registration, the value of the optical path length difference for the two parts of the optical radiation propagating through the optical means 122 is set substantially equal to the first value. In this embodiment, the same as in above mentioned, the optical means 122 includes means adapted for changing the optical path length difference for the two parts of the optical radiation (not shown in the drawing), for obtaining the in-depth profile of the reflected sample portion of the optical radiation. Thus, a combination optical radiation, responsive to a portion of the reflected or backscattered optical radiation that is not depolarized by the associated sample 106, is registered. As will be appreciated by a skilled artisan, the depolarized portion of the optical radiation reflected or backscattered from the associated sample 106 does not produce interference fringes and is not registered.

For selecting a cross-polarized component of the combined optical radiation using frequency domain registration, the value of the optical path length difference for the two parts of the optical radiation propagating through the optical means 122 is, preferably, selected from the group consisting of: less than the difference between the first value and the third value, and exceeds the sum of the second value and the third value. As will be recognized by those skilled in the art, the value of the optical path length difference being less than the difference between the first value and the third value, or exceeding the sum of the second value and the third value, nonetheless stays in the vicinity of the value of the reference offset.

The optical spectrum of the combination optical radiation registered by the optoelectronic registering means 124, when frequency domain registration is provided, has all necessary information about the in-depth coherent reflection profile by including a component that is Fourier conjugate of the in-depth profile of an associated sample 106. No depth ambiguity problem arises since the optical path difference for the interfering reference and any part of the sample portion belonging to the longitudinal range of interest 136 for the parts of the optical radiation propagating along optical paths 126, 126, is not reduced to zero. Thus, the profile is extracted from Fourier transformation of the optical spectrum of the combined optical radiation by the data processing and displaying unit of the optoelectronic registering means 124.

As will be appreciated by a skilled artisan, for selecting a cross-polarized component of the combined optical radiation using frequency domain registration, the value of the optical path length difference for the two parts of the optical radiation propagating through the optical means 122 is also capable of being selected between the sum of the second value and the third value, and the difference between the first value and the third value. In this embodiment, at least one of the optical paths 126, 128 of the optical means 122 includes means for eliminating mirror ambiguity, DC artifacts, and autocorrelation artifacts. One skilled in the art will recognize that such means are well known in the art, and any such means is capable of being suitably included in at least one of the optical paths 126, 128. For example and without limitation, a phase modulator or a frequency modulator advantageously included in one of the optical paths 126, 128 of the optical means 122 (not shown in the drawing), substantially eliminates mirror ambiguity, DC artifacts, and autocorrelation artifacts, and improves the SNR of the reflectometer 100 of the subject application, as well.

For selecting a parallel-polarized component of the combined optical radiation using frequency domain registration, the value of optical path length difference for the two parts of the optical radiation propagating through the optical means 122 is, preferably, selected from the group consisting of: less than the first value, and exceeds the second value. As will be appreciated by those skilled in the art, the value of optical path length difference for the two parts of the optical radiation propagating through the optical means 122 is also capable of being selected between the first value and the second value. In this embodiment, at least one of the optical paths 126, 128 of the optical means 122 includes means for eliminating mirror ambiguity, DC artifacts, and autocorrelation artifacts (not shown in the drawing).

In another preferred embodiment, the optoelectronic selecting means 120 is capable of simultaneously selecting a parallel-polarized component and a cross-polarized component of the combined optical radiation representative of an optical radiation having returned from an associated sample 106. In this embodiment, for time domain registration the value of the optical path length difference for the two parts of the optical radiation propagating through the optical paths 126, 128 in the optical means 122 is selected substantially equal to the first value, whereas the scanning range is selected substantially equal to a double the scanning range necessary for selecting only one component the combined optical radiation. As will be recognized by those skilled in the art, the double the scanning range is substantially equal to a double longitudinal range of interest 136. Those skilled in art will appreciate that the value of the optical path length difference for the two parts of the optical radiation is also capable of being selected substantially equal to the second value. However, in this embodiment, the optical path length difference of the optical paths 126, 128 for obtaining the time profile of the combined optical radiation, is scanned in the opposite direction with respect to the previous embodiment.

For simultaneous frequency domain registration of a parallel-polarized component and of a cross-polarized component of the combined optical radiation representative of an optical radiation having returned from an associated sample 106, the value of the optical path length difference for the two parts of the optical radiation propagating through the optical paths 126, 128 in the optical means 122 is selected from the group of: less than the first value, or exceeding the second value. Those skilled in the art will recognize that the value of the optical path length difference is also capable of being selected between the first and second value. However in this embodiment, at least one of the optical paths 126, 128 of the optical means 122 includes a device for eliminating mirror ambiguity, DC artifacts, and autocorrelation artifacts. As will be further recognized by those skilled in the art, for simultaneous frequency domain registration of parallel-polarized and cross-polarized components of the combined optical radiation, the effective scanning range is to be set double that of the effective scanning range for registering just one component (parallel-polarized, or cross-polarized) of the combined optical radiation. A skilled artisan will further appreciate that, no actual scanning being necessarily performed for frequency domain registration, the effective scanning range is determined by the spectral resolution and sampling of the frequency domain optical coherence reflectometry/tomography engine.

Referring now to operation of the polarization sensitive common path optical coherence reflectometer 200 in accordance with the present invention shown in FIG. 2, the operation of the reflectometer 200 commences and initially proceeds essentially, in the same manner as the operation of the reflectometer 100 depicted in FIG. 1, as described in detail above. The reflectometer 200 of the subject application is specified by an optical path length difference of a first value for an optical radiation beam propagating to the reference reflector (the tip 216 of the optical fiber 210) and to the proximal boundary 256 of the longitudinal range of interest 254. The reflectometer 200 is further specified by an optical path length difference of a second value for the optical radiation beam propagating to the reference reflector (the tip 216 of the optical fiber 210) and to the distal boundary 258 of a longitudinal range of interest 256. The reflectometer 200 is further specified by an optical path length difference of a third value for the replicas of the optical radiation propagating through the converting means 204.

In contrast to the operation of the reflectometer 100, the combination optical radiation returning from the optical fiber probe 208, after passing through the directional element 220 enters the directional splitting means 218. The combination optical radiation is split by the directional splitting means 218 into two parts. One part of the combination optical radiation is directed to the first optoelectronic selecting means 222, wherein another part of the combined optical radiation is directed to the second optoelectronic selecting means 224.

The operation of the first and second optoelectronic selecting means 222, 224, respectively, is analogous to that described with reference to the optoelectronic selecting means 120 as depicted in FIG. 1. The first optoelectronic selecting means 222 is adapted for selecting a cross-polarized component of the combined optical radiation representative of an optical radiation having returned from an associated sample 206. The second optoelectronic selecting means 224 is adapted for selecting a parallel-polarized component of the combined optical radiation representative of an optical radiation having returned from an associated sample 206. Both components are capable of being selected by using time domain or frequency domain registration. Those skilled in art will appreciate that a selection of a desired component of the combined optical radiation by optoelectronic selecting means 222, 224, as well as time domain or frequency domain registration of these components, is subject to an optical path length difference for the combined optical radiation in optical means 226, 230, and is provided analogous to that as described in detail with reference to the reflectometer shown in FIG. 1.

Referring now to operation of the polarization sensitive common path optical coherence reflectometer 600 in accordance with the present invention shown in FIG. 6, the operation of the reflectometer 600 commences analogous to that described with reference reflectometers of FIG. 1, and FIG. 2, by placing the delivering device, preferably implemented as an optical fiber probe 608, at a predetermined distance with respect to the proximal boundary 638 of the longitudinal range of interest 636. This distance will be referred to hereinafter as an optical path length of a first value (reference offset). The distance between the tip 614 of the optical fiber 608 and the distal boundary 640 of the longitudinal range of interest 636, will be referred to hereinafter as an optical path length of a second value.

Next, a polarized optical radiation from the source 602 is directed to the optical fiber probe 604 through the directional element 616. The optical fiber probe 604 is adapted for forming and delivering an optical radiation beam to an associated sample 606. Thus, one part of the optical radiation beam is delivered to an associated sample 606 and is reflected or backscattered from it (the sample portion). Assuming the optical properties of an associated sample 606 such that they have an influence on the polarization state of the incident optical radiation, the optical radiation reflected or backscattered from an associated sample 606 has a polarization state which differs from that of the incident optical radiation. As will be recognized by those skilled in the art, the optical radiation reflected or backscattered from an associated sample 606 includes a superposition of two mutually coherent orthogonal components. It will be also apparent to those skilled in the art that of the two mentioned mutually coherent orthogonal components, one is parallel-polarized with respect to the polarization state of the incident sample portion, whereas the other component is cross-polarized with respect to the incident sample portion. The magnitudes of the components are subject to the depolarization influence of an associated sample 606.

Another part of the optical radiation beam of the optical radiation that enters the optical fiber probe 604 does not reach an associated sample 606, but is instead reflected at the tip 614 of optical fiber 608 of the optical fiber probe 604, at some distance from an associated sample 606 (the reference portion). Obviously, the optical properties of an associated sample 606 have no influence on the polarization state of the reference portion of the optical radiation. Thus, the polarization state of the reference portion will remain the same as that of the incident optical radiation.

The optical radiation returning from the optical fiber probe 604 is a combination of the reference portion and the reflected or backscattered sample portion shifted axially. As will be recognized by those skilled in the art, the polarization state relationship between respective portions of optical radiation does not change as the replicas propagate through the optical fiber probe 604, since all portions of the optical radiation propagate through the same optical path. This combined optical radiation is directed through the directional element 616 to the converting means 620, which is part to the optoelectronic selecting means 618. The directional element 616, the same as the optical fiber probe 604, has no influence on the polarization state relationship between respective portions of optical radiation.

The element 628 of the converting means 620 splits the combined optical radiation, incoming from the optical fiber probe 604 through the directional element 616, into two parts of the optical radiation. In other words, the sample portion and the reference portion of the optical radiation incoming from the optical fiber probe 604, is split each into two parts by the element 628. One part of the sample and reference portions propagates along the optical path 624 in a forward direction and after being reflected by the regular mirror 632 returns to the element 628. The other part of the sample and reference portions that propagates along the optical path 626, passes through the polarization controller 630 in a forward direction and after being reflected by the regular mirror 634 passes through the polarization controller 630 in a backward direction, thus returning to the element 630.

In one embodiment, the converting means 620 implements a regular single mode optical fiber, which does not maintain the initial polarization state of the optical radiation. Hence, a random polarization change occurs in the optical path 624 and in the optical path 626 for all portions of the optical radiation. However, the polarization controller 630 included in the optical path 626, converts the polarization state of the reference portion propagating through the optical path 626 such, that when entering the element 630, this reference portion is cross-polarized with respect to the reference portion entering the element 630 from the optical path 624.

Those skilled in art will recognize that the polarization controller 630 is capable of being adjusted once after all fiber is packaged, to compensate for all stress-induced birefringence. Those skilled in the art will further appreciate that optical radiations having parallel polarizations interfere and those having orthogonal polarizations do not interfere. Hence, a corresponding component of the sample portion having returned to the element 628 from the optical path 626, will interfere with the reference portion returning to the element 628 from the optical path 624, since the reference portion after being reflected from the regular mirror 632 has, at the element 628, the same polarization, as one of the components of the sample portion that returned from the optical path 626, and vice versa. Thus, the optoelectronic selecting means 618 selects a cross-polarized component of the combined optical radiation representative of an optical radiation having returned from an associated sample 606. Depending on the value of the preset optical path length difference for the parts of the optical radiation propagating along respective optical paths 624, 626, frequency domain or time domain registration is capable of being provided.

As mentioned above, the reflectometer 600 of the subject application is specified by an optical path length difference of a first value for an optical radiation beam propagating to the reference reflector (the tip 614 of the optical fiber 608) and to the proximal boundary 638 of the longitudinal range of interest 636. The reflectometer 600 is further specified by an optical path length difference of a second value for the optical radiation beam propagating to the reference reflector (the tip 614 of the optical fiber 608) and to the distal boundary 640 of a longitudinal range of interest 636.

For employing time domain registration, the value of the optical path length difference for the two parts of the optical radiation propagating through the converting means 620 is selected substantially equal to the first value. In this embodiment, the converting means 620 includes means adapted for changing the optical path length difference for the two parts of the optical radiation (not shown in the drawing). By scanning the optical path length difference of the optical paths 624, 626 the time profile of the combined optical radiation is obtained. Those skilled in the art will recognize that the scanning range is substantially equal to the longitudinal range of interest 636. This time profile represents the in-depth profile of the reflected sample portion of the optical radiation. For example and without limitation, a PZT fiber delay element is capable of being used for scanning the optical path length difference, which can be inserted in one or both optical paths 624, 626. The obtained combined signal is equivalent to the interference signal from an "orthogonal" registration channel in previously known polarization sensitive OCT devices. Those skilled in the art will appreciate that the value of the optical path length difference for the two parts of the optical radiation propagating through the converting means 620 is capable of being selected substantially equal to the second value. As will be evident to a skilled artisan, in this embodiment, scanning the optical path length difference is provided in an opposite direction, with respect to the above described embodiment.

For employing frequency domain registration, the value of the optical path length difference for the two parts of the optical radiation propagating through the converting means 620 is, preferably, selected from the group consisting of: less than the first value, and exceeds the second value. As will be recognized by those skilled in the art, the value of the optical path length difference stays in the vicinity of the value of the reference offset.

The optical spectrum of the combination optical radiation registered by the optoelectronic registering means 622, when frequency domain registration is provided, has all necessary information about the in-depth coherent reflection profile by including a component that is Fourier conjugate of the in-depth profile of an associated sample 606. No depth ambiguity problem arises since the optical path difference for the interfering reference and any part of the sample portion belonging to the longitudinal range of interest 636 for the parts of the optical radiation propagating along optical paths 624, 626, is not reduced to zero. Thus, the profile is extracted from Fourier transformation of the optical spectrum of the combined optical radiation by the data processing and displaying unit of the optoelectronic registering means 622.

As will be appreciated by a skilled artisan, for selecting a cross-polarized component of the combined optical radiation using frequency domain registration, the value of the optical path length difference for the two parts of the optical radiation propagating through the converting means 620 is also capable of being selected between the first value and the second value. In this embodiment, at least one of the optical paths 624, 626 of the converting means 620 includes a device for eliminating mirror ambiguity, DC artifacts, and autocorrelation artifacts. One skilled in the art will recognize that such devices are well known in the art, and any such device is capable of being suitably included in at least one of the optical paths 624, 626.

For example and without limitation, a phase modulator or a frequency modulator advantageously included in one of the optical paths 624, 626 of the converting means 620 (not shown in the drawing), substantially eliminates mirror ambiguity, DC artifacts, and autocorrelation artifacts, and improves the SNR of the reflectometer 600 of the subject application, as well.

Referring now to operation of the polarization sensitive common path optical coherence reflectometer 700 in accordance with the present invention shown in FIG. 7, the operation of the reflectometer 700 commences and initially proceeds essentially, in the same manner as the operation of the reflectometer 600 depicted in FIG. 6, as described in detail above. The reflectometer 700 of the subject application is specified by an optical path length difference of a first value for an optical radiation beam propagating to the reference reflector (the tip 716 of the optical fiber 708) and to the proximal boundary 756 of the longitudinal range of interest 754. The reflectometer 700 is further specified by an optical path length difference of a second value for the optical radiation beam propagating to the reference reflector (the tip 716 of the optical fiber 708) and to the distal boundary 758 of a longitudinal range of interest 756.

In contrast to the operation of the reflectometer 600, the combination optical radiation returning from the optical fiber probe 708, after passing through the directional element 716 enters the directional splitting means 718. The combination optical radiation is split by the directional splitting means 718 into two parts. One the part of the combination optical radiation is directed to the first optoelectronic selecting means 720, wherein another part of the combined optical radiation is directed to the second optoelectronic selecting means 722. The first optoelectronic selecting means 720 is adapted for selecting a cross-polarized component of the combined optical radiation representative of an optical radiation having returned from an associated sample 706. The second optoelectronic selecting means 722 is adapted for selecting a parallel-polarized component of the combined optical radiation representative of an optical radiation having returned from an associated sample 706.

Both components are capable of being selected by using time domain or frequency domain registration. Those skilled in art will appreciate that a selection of a desired component of the combined optical radiation by optoelectronic selecting means 720, 722, as well as time domain or frequency domain registration of these components, is subject to an optical path length difference for the combined optical radiation in the converting means 724 and optical means 722.

The operation of the first optoelectronic selecting means 720 is analogous to that described with reference to the optoelectronic selecting means 618 as depicted in FIG. 6. Those skilled in the art will recognize that the second optoelectronic selecting means 722 operates, essentially, in the same manner as the optoelectronic selecting means 120 described above with reference to the reflectometer of FIG. 1. However, for employing time domain registration, the value of the optical path length difference for the two parts of the optical radiation propagating through the optical means 740 is selected substantially equal to the first value. For employing frequency domain registration, the value of the optical path length difference for the two parts of the optical radiation propagating through the optical means 740 is, preferably, selected from the group consisting of: less than the first value, and exceeds the second value.

As will be recognized by those skilled in the art, the embodiments depicted in FIG. 6 and FIG. 7, are efficient when a polarization state of the optical radiation at the output of the directional element 616, 716, respectively, does not change during the system operation or maintainance. The latter is capable of being achieved by either of (a) a Faraday element in the distal tip of the probe, compensating for all dynamic birefringence in the probe fiber (not shown in the drawings); (b) building the entire system using polarization maintaining fiber, so initially launched polarization will maintain it's orientation; or (c) having a configuration when the optical fiber is maintained in an enclosure and is not bent or flexed during operation of the reflectometer.

The preceding embodiments and methodologies will be better understood when viewed in conjunction with the examples of producing a combination optical radiation depicted in FIGS. 8a, 8b and 8c and FIGS. 9a, 9b and 9c.

Figure 8A:
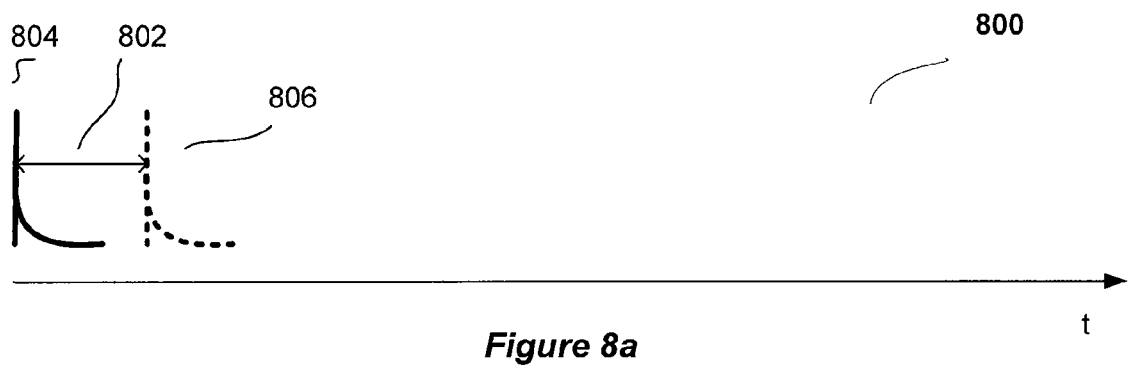
FIGS. 8a, 8b and 8c are illustrations of producing a combination optical radiation in one embodiment of the invention in accordance with the subject application.
Figure 8B:
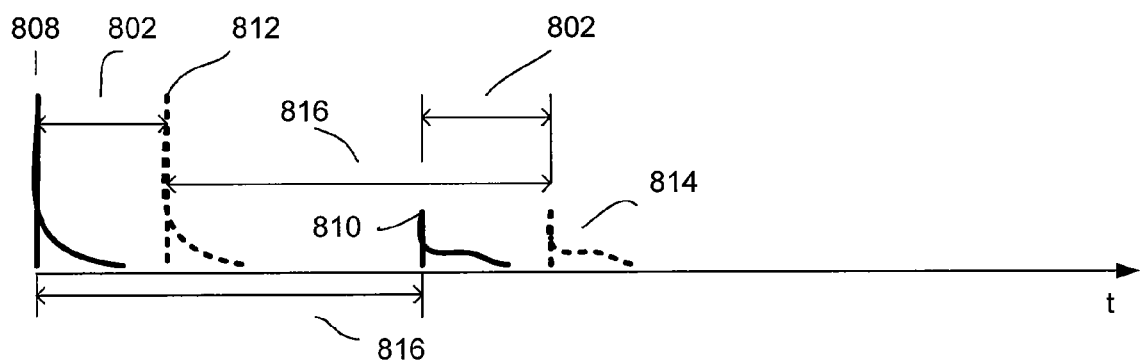
Figure 8C:
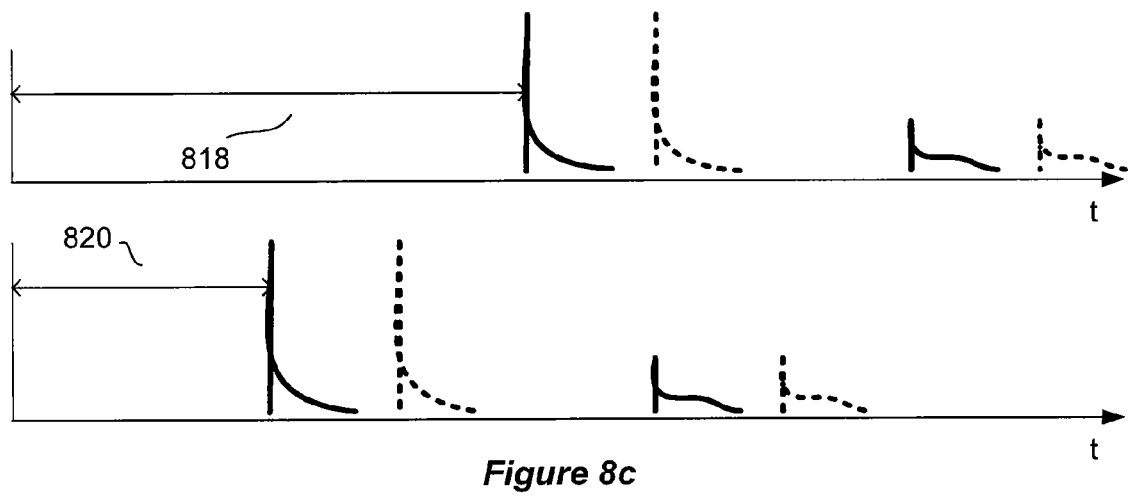

Turning now to FIGS. 8a, 8b and 8c, there is shown an illustration 800 of producing a combination optical radiation in an embodiment of the invention depicted in FIG. 1. For illustration purposes the optical radiation is represented by imaginary short pulses propagating therethrough and placed along a time axis t in FIGS. 8a, 8b and 8c. Thus, FIG. 8a illustrates the optical radiation entering the optical fiber probe 108 through the directional element 118 of FIG. 1, after the optical radiation incoming from the source of optical radiation 102 is converted into two cross-polarized replicas of the optical radiation, propagating therethrough with a predetermined optical path length difference 802. The two replicas are illustrated in FIG. 8a as respective short pulses 804 and 806 shifted along the time axis by converting means 104, whereby the replica 806 illustrated by a dotted line, is cross-polarized with respect to the replica 804. As will be appreciated by those skilled in the art, both replicas experience a change in the own polarization state as the optical radiation propagates through the optical fiber probe 108, however they maintain the relative polarization state, e.g. orthogonality.

FIG. 8b further illustrates the two replicas entering the optical means 122 after each of them was split into two portions (a reference portion and a sample portion) by the tip 116 of the optical fiber 110 of the optical fiber probe 108. As shown in FIG. 8b, the replica 804 is split into a reference portion 808 and a sample portion 810, whereas the replica 806 is split into a reference portion 812 and a sample portion 814. The reference portion 808 of the replica 804 has a shift (reference offset 816) with respect to the sample portion 810 of the same replica. Also, the reference portion 812 of the replica 806 has a shift (reference offset 816) with respect to the sample portion 814 of the same replica. As will be apparent to a skilled artisan, and as illustrated in FIGS. 8a, 8b and 8c, both the reference portions 808, 812 and the sample portions 810, 814 of the two replicas, maintain the initial optical path length difference 802. Those skilled in the art will appreciate that the replicas illustrated in FIGS. 8a, 8b and 8c correspond to a part of the optical radiation propagating along one of the optical paths.

Further illustrated in FIG. 8c is the selection of a cross-polarized component of the combined optical radiation, when the optical path difference 818 for the two parts of the optical radiation propagating through the optical means 122 is substantially equal to the sum of the reference offset 816 and the optical path difference 802 between the cross-polarized replicas outgoing from the converting means 104. Those skilled in the art will appreciate that the reference portion 820 of one replica interferes with a corresponding component of the sample portion 814 of the other replica.

Further illustrated in FIG. 8c is the selection of a cross-polarized component of the combined optical radiation, when the optical path difference 822 for the two parts of the optical radiation propagating through the optical means 122 is substantially equal to the difference between the reference offset 816 and the optical path difference 802 between the cross-polarized replicas outgoing from the converting means 104. Those skilled in the art will appreciate that the reference portion 824 of one replica interferes with a corresponding component of the sample portion 810 of the other replica.

Figure 9A:
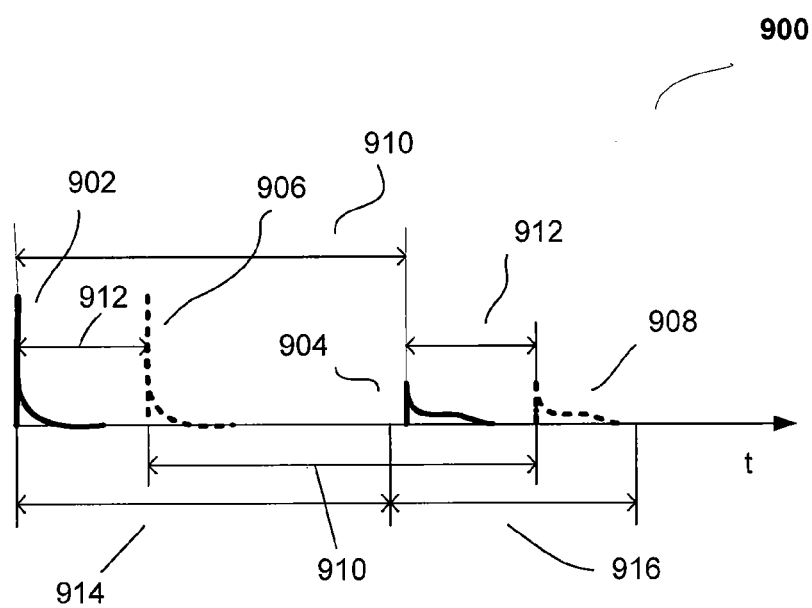
FIGS. 9a, 9b and 9c are illustrations of producing a combination optical radiation in another embodiment of the invention in accordance with the subject application.
Figure 9B:
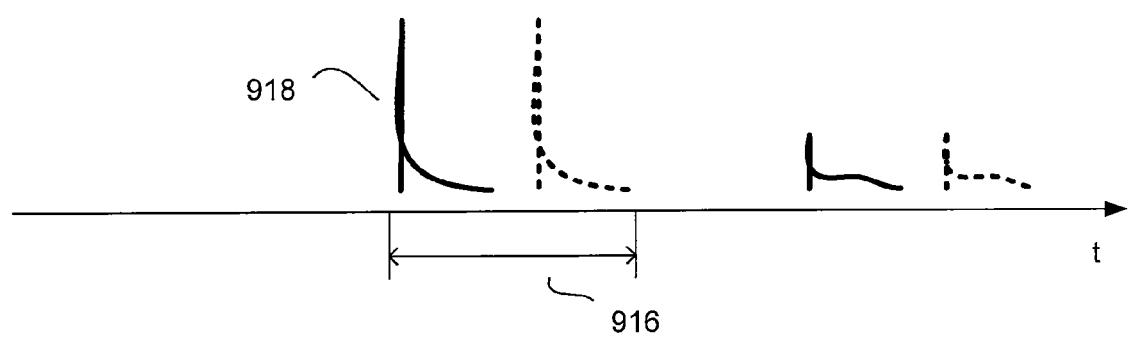
Figure 9C:
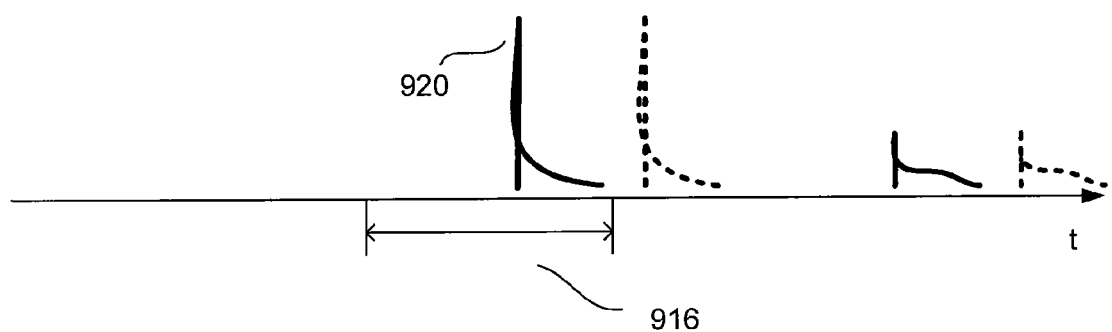

Turning now to FIGS. 9*a*, 9*b* and 9*c*, there is shown another illustration 900 of producing a combination optical radiation in an embodiment of the invention depicted in FIG. 1. FIG. 9*a* illustrates the two replicas of optical radiation entering the optical means 122 after each of them was split into two portions (a reference portion and a sample portion) by the tip 116 of the optical fiber 110 of the optical fiber probe 108. As shown in FIG. 9*a*, one replica is split into a reference portion 902 and a sample portion 904, whereas the other replica is split into a reference portion 906 and a sample portion 908. The portions of the second replica are illustrated by dotted lines. The reference portion 902 of the first replica has a shift (reference offset 910) with respect to the sample portion 904 of the same replica. Also, the reference portion 906 of the second replica has a shift (reference offset 910) with respect to the sample portion 908 of the same replica. Those skilled in the art will recognize that the reference potions 902, 906, as well as the sample portions 904, 908 of the two replicas, have an optical path length difference 912.

Further shown in FIG. 9*b* and FIG. 9*c* is an intermediate stage of the in-depth scanning cycle for the same configuration. Here the optical path difference 914 for the two parts of the optical radiation propagating through the optical means 122, which is substantially equal to the reference offset 910, and the scanning range 916 which is substantially equal to a double longitudinal range of interest 136. Those skilled in art will appreciate that, as illustrated in FIG. 9*b*, the reference portion 918 of the optical radiation propagating through the optical path 126 of optical means 122 interferes with a respective component of the sample portion 904 of the optical radiation propagating through the optical path 128 of optical means 122. Thereby, a parallel-polarized component is selected, since the interfering portions originate from the same initial replica. Simultaneously, the reference portion 920 (FIG. 9*c*) of the optical radiation propagating through the optical path 126 of optical means 122 interferes with a respective component of the sample portion 908 of the optical radiation propagating through the optical path 128 of optical means 122. Thereby, a cross-polarized component is selected, since the interfering portions originate from cross-polarized initial replicas. Thus, a parallel-polarized component and a cross-polarized component of the combined optical radiation representative of an optical radiation having returned from an associated sample 106, are capable of being simultaneously selected.

The foregoing description of the preferred embodiments of the subject application has been presented for purposes of illustration and description. It is not intended to be exhaustive or to limit the subject application to the precise form disclosed. Obvious modifications or variations are possible in light of the above teachings. The embodiments were chosen and described to provide the best illustration of the principles of the subject application and its practical application to thereby enable one of ordinary skill in the art to use the subject application in various embodiments and with various modifications as are suited to the particular use contemplated. All such modifications and variations are within the scope of the subject application as determined by the appended claims when interpreted in accordance with the breadth to which they are fairly, legally and equitably entitled.

What is claimed is:

1. A polarization sensitive common path optical coherence reflectometer comprising:
    a source of optical radiation;
    a converting device optically coupled with the source of optical radiation, the converting device configured to produce at least two cross-polarized replicas of the optical radiation incoming from the source of optical radiation, propagating therethrough with a predetermined optical path length difference;
    a delivering device that delivers an optical radiation beam including the at least two cross-polarized replicas to an associated sample, the delivering device including a proximal part and a distal part, the distal part of the delivering device including a polarization insensitive reference reflector, the delivering device being further configured to produce a combined optical radiation representative of an optical radiation having returned from an associated sample, the combined optical radiation being a combination of an optical radiation having returned from an associated sample and of an optical radiation reflected from the reference reflector;
    a directional element optically coupled with the converting device and optically coupled with the proximal part of the delivering device, the directional element being configured to direct optical radiation to the delivering device; and
    an optoelectronic selecting device optically coupled with the directional element, the optoelectronic selecting device including an optical device optically coupled with an optoelectronic registering device;
    wherein the optical device is configured to split the combined optical radiation, incoming from the delivering device through the directional element, into at least two parts of the optical radiation propagating therethrough with a preset optical path length difference, and further recombining the at least two parts of the optical radiation, and wherein the optoelectronic registering device is positioned to receive the recombined optical radiation from the optical device; and
    wherein the optoelectronic selecting device is configured to select at least one of the following: a cross-polarized component of the combined optical radiation representative of an optical radiation having returned from an associated sample, and a parallel-polarized component of the combined optical radiation representative of an optical radiation having returned from an associated sample, subject to the preset optical path length difference for the at least two portions of the optical radiation propagating through the optical device.

2. A polarization sensitive common path optical coherence reflectometer of claim 1 wherein the converting device comprises:
    at least two optical paths; and
    at least one element configured to split the optical radiation, incoming from the source of optical radiation into two replicas of the optical radiation and thereafter recombining the two replicas of the optical radiation having propagated along respective optical paths in a forward and backward direction;
    wherein each optical path includes a mirror at its end;
    wherein at least one of the at least two optical paths includes a polarization controller configured to control the polarization state of an associated replica of the optical radiation; and
    wherein the at least two optical paths have a predetermined optical path length difference for the two replicas of the optical radiation.

3. A polarization sensitive common path optical coherence reflectometer of claim 1 wherein the converting device comprises:
- at least two optical paths;
- at least one element configured to split the optical radiation, incoming from the source of optical radiation into two replicas of the optical radiation; and
- at least one element configured to recombine the two replicas of the optical radiation having propagated along respective optical paths in a forward direction;
- wherein at least one of the at least two optical paths includes a polarization controller configured to control the polarization state of an associated replica of the optical radiation; and
- wherein the at least two optical paths have a predetermined optical path length difference for the two replicas of the optical radiation.

4. A polarization sensitive common path optical coherence reflectometer of claim 1 wherein the converting device comprises:
- a portion of polarization maintaining optical fiber configured to produce two cross-polarization modes of the optical radiation propagating therethrough with a predetermined optical path length difference; and
- a polarization controller placed between the source of optical radiation and the portion of polarization maintaining optical fiber;
- wherein the polarization controller is configured to control a power ratio between the two cross-polarization modes of the optical radiation propagating through the portion of polarization maintaining optical fiber.

5. The polarization sensitive common path optical coherence reflectometer of claim 1 wherein the optoelectronic registering device is a time domain optoelectronic registering device configured to change the optical path length difference for the two parts of the optical radiation.

6. The polarization sensitive common path optical coherence reflectometer of claim 1 wherein the optoelectronic registering device is a frequency domain optoelectronic registering device.

7. The polarization sensitive common path optical coherence reflectometer of claim 1 wherein the optical device comprises:
- at least two optical paths; and
- at least one polarization insensitive element configured to split the combined optical radiation, incoming from the delivering device through the directional element, into two parts of the optical radiation and thereafter recombining the two parts of the optical radiation having propagated along respective optical paths in a forward and backward direction;
- wherein each optical path includes a Faraday mirror at its end; and
- wherein the at least two optical paths have a preset optical path length difference for the two parts of the optical radiation.

8. A polarization sensitive common path optical coherence reflectometer comprising:
- a source of optical radiation;
- a converting device optically coupled with the source of optical radiation, the converting device configured to produce at least two cross-polarized replicas of the optical radiation incoming from the source of optical radiation and propagating therethrough with an optical path length difference;
- a delivering device configured to form and deliver an optical radiation beam to an associated sample, the delivering device including a proximal part and a distal part, the distal part of the delivering device including a reference reflector, the delivering device being further configured to produce a combined optical radiation representative of an optical radiation having returned from an associated sample, the combined optical radiation being a combination of an optical radiation having returned from an associated sample and of an optical radiation reflected from the reference reflector;
- a directional splitting device;
- a directional element optically coupled with the converting device, with the proximal part of the delivering device, and with the directional splitting device, the directional element being configured to direct optical radiation to the delivering device and being configured to direct optical radiation to the directional splitting device;
- a first optoelectronic selecting device optically coupled with the directional splitting device, the first optoelectronic selecting device including a first optical device optically coupled with a first optoelectronic registering device; and
- a second optoelectronic selecting device optically coupled with the directional splitting device, the second optoelectronic selecting device including a second optical device optically coupled with a second optoelectronic registering device;
- wherein the directional splitting device is configured to split the combined optical radiation, incoming from the directional element into two fractions, directing one fraction of the combined optical radiation to the first optoelectronic selecting device, and directing another fraction of the combined optical radiation to the second optoelectronic selecting device, and wherein the first optoelectronic registering device is positioned to receive the recombined optical radiation from the first optical device;
- wherein the first optical device is configured to split the part of combined optical radiation, incoming from the delivering device through the directional element and the directional splitting device, into at least two parts of the optical radiation propagating therethrough with a first preset optical path length difference, and further recombining the at least two parts of the optical radiation, and wherein the second optoelectronic registering device is positioned to receive the recombined optical radiation from the second optical device;
- wherein the second optical device is configured to split the part combined optical radiation, incoming from the delivering device through the directional element and the directional splitting device, into at least two parts of the optical radiation propagating therethrough with a second preset optical path length difference, and further recombining the at least two parts of the optical radiation;
- wherein the first optoelectronic selecting device is configured to select a cross-polarized component of the combined optical radiation representative of an optical radiation having returned from an associated sample; and
- wherein the second optoelectronic selecting device is configured to select a parallel-polarized component of the combined optical radiation representative of an optical radiation having returned from an associated sample.

9. The polarization sensitive common path optical coherence reflectometer of claim 8 wherein the first and second optical devices each comprises:
- at least two optical paths; and at least one polarization insensitive element configured to split the part of combined optical radiation, incoming from the delivering device through the directional element and the directional splitting device, into two replicas of the optical radiation and thereafter recombining the two replicas of the optical radiation having propagated along respective optical paths in a forward and backward direction;

wherein each optical path includes a Faraday mirror at its end; and wherein the at least two optical paths in the first and second optical devices have a respective preset optical path length difference for the respective two parts of the optical radiation.

10. The polarization sensitive common path optical coherence reflectometer of claim 8 wherein the first and second optoelectronic registering devices each is a time domain optoelectronic registering device configured to change the optical path length difference for the two respective parts of the optical radiation.

11. The polarization sensitive common path optical coherence reflectometer of claim 8 wherein the first and second optoelectronic registering device each is a frequency domain optoelectronic registering device.

12. A polarization sensitive common path optical coherence reflectometer comprising:

a source of optical radiation;

a delivering device configured to form and deliver an optical radiation beam to an associated sample, the delivering device including a proximal part and a distal part, the distal part of the delivering device including a reference reflector, the delivering device being further configured to produce a combined optical radiation representative of an optical radiation having returned from an associated sample, the combined optical radiation being a combination of a sample portion of the optical radiation having returned from an associated sample and of a reference portion of the optical radiation reflected from the reference reflector;

a directional element optically coupled with the source of optical radiation and with the proximal part of the delivering device, the directional element being configured to direct optical radiation to the delivering device; and first optoelectronic selecting device optically coupled with the directional element and including a converting device optically coupled with first optoelectronic registering device;

wherein the converting device is configured to split the sample portion and the reference portion of the combined optical radiation incoming from the delivering device through the directional element, into at least two parts of optical radiation propagating therethrough with a first preset optical path length difference, and further recombining the at least two parts of the optical radiation, and wherein the first optoelectronic registering device is positioned to receive the recombined optical radiation from the converting device;

wherein the converting device is further configured to convert the reference portion of at least one part of the optical radiation such that the reference portions of the at least two parts of the optical radiation are cross-polarized portions of optical radiation; and wherein the first optoelectronic selecting device is configured to select a cross-polarized component of the combined optical radiation representative of an optical radiation having returned from an associated sample.

13. A polarization sensitive common path optical coherence reflectometer of claim 12 wherein the converting device comprises:

at least two optical paths; and at least one first polarization insensitive element configured to split the combined optical radiation, incoming from the delivering device, into two parts of the optical radiation and thereafter recombining the two parts of the optical radiation having propagated along respective optical paths in a forward and backward direction;

wherein at least one of the at least two optical paths includes a polarization controller configured to control the polarization state of an associated portion of the optical radiation, and a regular mirror at its end;

wherein the other of the at least two optical paths includes a mirror at its end; and wherein the at least two optical paths have a first preset optical path length difference for the two parts of the optical radiation.

14. A polarization-sensitive common path optical coherence reflectometer of claim 12 further comprising:

a directional splitting device;

a second optoelectronic selecting device optically coupled with the directional splitting device and including an optical device optically coupled with a second optoelectronic registering device;

wherein the optical device is configured to split the combined optical radiation, incoming from the delivering device through the directional element and the directional splitting device, into at least two parts of the optical radiation propagating therethrough with a second preset optical path length difference, and further recombining the at least two parts of the optical radiation;

wherein the directional element is in optical communication with the first optoelectronic selecting device and with the second optoelectronic selecting device through the directional splitting device;

wherein the directional splitting device is configured to split the combined optical radiation into two fractions of the combined optical radiation;

wherein the directional splitting device is further configured to direct one fraction of the combined optical radiation to the first optoelectronic selecting device, and to direct another fraction of the combined optical radiation to the second optoelectronic selecting device; and wherein the second optoelectronic selecting device is adapted for selecting a parallel-polarized component of the combined optical radiation representative of an optical radiation having returned from an associated sample.

15. The polarization sensitive common path optical coherence reflectometer of claim 14 wherein the optical device comprises:

at least two optical paths; and at least one polarization insensitive element configured to split the combined optical radiation, incoming from the delivering device through the directional element, into two parts of the optical radiation and thereafter recombining the two parts of the optical radiation having propagated along respective optical paths in a forward and backward direction;

wherein each optical path includes a Faraday mirror at its end; and wherein the at least two optical paths have a second preset optical path length difference for the two parts of the optical radiation.

16. The polarization sensitive common path optical coherence reflectometer of claim 12 wherein the first and second optoelectronic registering devices each is a time domain optoelectronic registering means configured to change the optical path length difference for the two respective parts of the optical radiation.

17. The polarization sensitive common path optical coherence reflectometer of claim 12 wherein the first and second optoelectronic registering device each is a frequency domain optoelectronic registering device.

* * * * *